(12) United States Patent
Cole et al.

(10) Patent No.: US 6,730,828 B1
(45) Date of Patent: May 4, 2004

(54) ISOLATED NUCLEIC ACIDS ENCODING A WHEAT GLUTATHIONE TRANSFERASE, PLANTS TRANSFORMED THEREWITH AND METHODS OF USE THEREOF

(75) Inventors: David J. Cole, Essex (GB); Ian Cummins, Durham (GB); Robert Edwards, Durham (GB)

(73) Assignee: Aventis Agriculture Limited, Essex (GB)

( * ) Notice: Subject to any disclaimer, the term of this patent is extended or adjusted under 35 U.S.C. 154(b) by 0 days.

(21) Appl. No.: 09/508,710

(22) PCT Filed: Sep. 16, 1998

(86) PCT No.: PCT/GB98/02802

§ 371 (c)(1),
(2), (4) Date: Jul. 10, 2000

(87) PCT Pub. No.: WO99/14337

PCT Pub. Date: Mar. 25, 1999

(30) Foreign Application Priority Data

Sep. 16, 1997  (GB) ................................. 971972

(51) Int. Cl.$^7$ .......................... A01H 5/00; C12N 15/29; C12N 15/82; C12N 15/54
(52) U.S. Cl. ................. 800/300; 435/320.1; 435/252.3; 435/419; 435/468; 536/23.6; 800/278
(58) Field of Search .................. 47/58.1; 435/320.1, 435/252.3, 468, 418, 419; 800/278, 300; 536/23.6, 23.1

(56) References Cited

U.S. PATENT DOCUMENTS 5,962,229 A * 10/1999 McGonigle et al.

FOREIGN PATENT DOCUMENTS

WO          9301294        1/1993

OTHER PUBLICATIONS

Riechers et al, Partial Characterization of Glutathione S–Transferases from Wheat (Triticu spp.) and Purification of a Safener–Induced Glutathione s–Transferase from Triticum tauschii, 1997, Plant Physiology, vol. 114, pp. 1461–1470.*

Dudler et al., 1991, Molecular Plant–Microbe Interactions, 4(1):14–18.

Fourgoux–Nicol et al 1999, Plant Molecular Biology, 40:857–872.

Duggleby 1997, Gene, 190:245–249.

Jepson et al., "Cloning and Characterization of maize herbicide safener–induced cDNAs encoding subunits of glutathione S–transferase isoforms I, II and IV", *Plant Mol. Biol.*, vol. 26 (1994) pp. 1855–1866.

Edwards, "Characterization of glutathione transferases and glutathione peroxidases in pea (Pisum sativum)", *Physiologia Plantarum*, vol. 98 (1996) pp. 594–604.

Cummins et al., "Purification of Multiple Glutathione Transferase Involved in Herbicide Detoxification from Wheat (Triticum aestivum L.) Treated with the Safener Fenchlorazole–ethyl", *Pesticide Biochemistry and Physiology*, vol. 59 (1997) pp. 35–49.

Riechers et al., "Partial Characterization of Glutathione S–Transferases from Wheat (Triticum spp.) and Purification of a Safener–Induced Glutathione S–Transferase from Triticum tauschii", *Plant Physiol.*, vol. 114 (1997) pp. 1461–1470.

Dixon et al., "Purification, regulation and cloning of a glutathione transferase (GST) from maize resembling the auxin–inducible type–III GSTs", *Plant Mol. Biol.*, vol. 36 (1998) pp. 75–87.

EMBL Database, Accession No. X79515, Feb. 28, 1995, 4 pages.

EMBL Database Accession No. Y12862, Jul. 30, 1997, 4 pages.

* cited by examiner

Primary Examiner—Amy J. Nelson
Assistant Examiner—David H Kruse
(74) Attorney, Agent, or Firm—Baker Botts L.L.P.

(57) ABSTRACT

This invention relates to isolated polynucleotides encoding a wheat glutathione transferase subunit (GST) as well as host cells and plants transformed therewith. The invention also relates to methods of using the isolated polynucleotides to make herbicide resistant plant cells and plants, and to methods of selecting transformed plant cells in the presence of an herbicide.

26 Claims, 2 Drawing Sheets

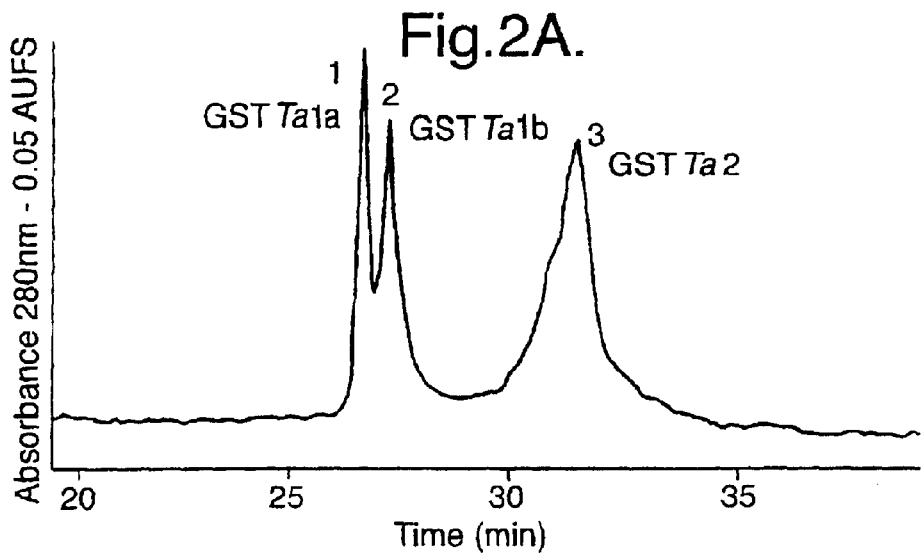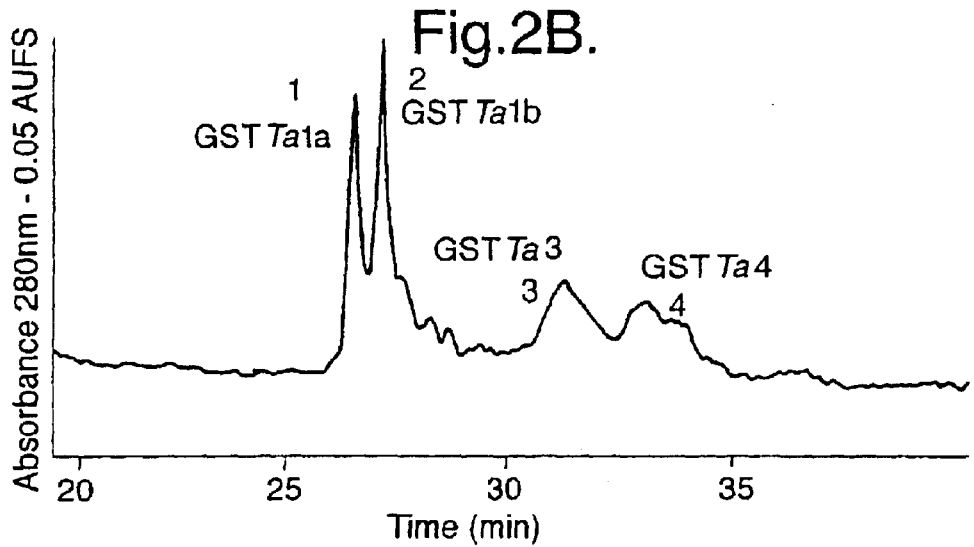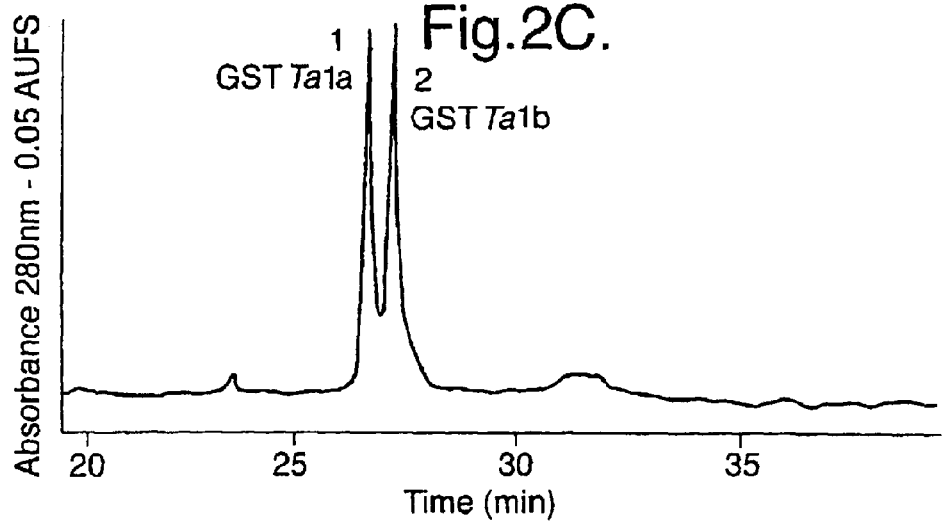

SEQUENCE LISTING

```
<160> NUMBER OF SEQ ID NOS:  19

<210> SEQ ID NO 1
<211> LENGTH: 1085
<212> TYPE: DNA
<213> ORGANISM: Triticum aestivum L.
<220> FEATURE:
<221> NAME/KEY: CDS
<222> LOCATION: (46)...(711)
<223> OTHER INFORMATION: Glutathione S transferase

<400> SEQUENCE: 1
caaacacaag cacagatcgg tcgagattca aggcaaccgg gagca atg gcg ggc gag      57
                                                 Met Ala Gly Glu
                                                   1 aag ggg ctg gtg ctg ctg gac ttc tgg gtg agc ccg ttc ggg cag cgc      105
Lys Gly Leu Val Leu Leu Asp Phe Trp Val Ser Pro Phe Gly Gln Arg
  5                  10                  15                  20
```

| | | |
|---|---|---|
| gtg cgc atc gcg ctg gcc gag aag ggc ctg ccc tac gag tac gcg gag<br>Val Arg Ile Ala Leu Ala Glu Lys Gly Leu Pro Tyr Glu Tyr Ala Glu<br>                   25                        30                     35 | 153 |
| gag gac ctg atg gcc ggc aag agc gac cgc ctc ctc cgc gcc aac ccg<br>Glu Asp Leu Met Ala Gly Lys Ser Asp Arg Leu Leu Arg Ala Asn Pro<br>            40                       45                     50 | 201 |
| gtg cat aag aag atc ccg gtg ctc ctc cac gac ggc cgt gcc gtc aac<br>Val His Lys Lys Ile Pro Val Leu Leu His Asp Gly Arg Ala Val Asn<br> 55                     60                     65 | 249 |
| gag tcc ctc atc atc ctc cag tac ctg gag gag gcc ttc ccg gac gcg<br>Glu Ser Leu Ile Ile Leu Gln Tyr Leu Glu Glu Ala Phe Pro Asp Ala<br>       70                     75                     80 | 297 |
| ccc gct ctg ctc ccc tcc gac ccc tac gcg cgc gcg cag gcc cgc ttc<br>Pro Ala Leu Leu Pro Ser Asp Pro Tyr Ala Arg Ala Gln Ala Arg Phe<br>85                     90                     95                100 | 345 |
| tgg gcc gac tac gtc gac aag aag gtc tac gac tgc ggc tcc cgc ctc<br>Trp Ala Asp Tyr Val Asp Lys Lys Val Tyr Asp Cys Gly Ser Arg Leu<br>                   105                   110                   115 | 393 |
| tgg aag ctc aag ggc gag ccg cag gcg cag gcg cgc gcc gag atg ctg<br>Trp Lys Leu Lys Gly Glu Pro Gln Ala Gln Ala Arg Ala Glu Met Leu<br>            120                     125                     130 | 441 |
| gac atc ctc aag acc ctc gac ggc gcg ctc ggg gac aag ccc ttc ttc<br>Asp Ile Leu Lys Thr Leu Asp Gly Ala Leu Gly Asp Lys Pro Phe Phe<br>               135                   140                   145 | 489 |
| ggc ggc gac aag ttc ggg ttc gtc gac gcc gcc ttc gcg ccc ttc acc<br>Gly Gly Asp Lys Phe Gly Phe Val Asp Ala Ala Phe Ala Pro Phe Thr<br>150                   155                   160 | 537 |
| gcg tgg ttc cac agc tac gag agg tac ggc gag ttc agc ctg ccg gag<br>Ala Trp Phe His Ser Tyr Glu Arg Tyr Gly Glu Phe Ser Leu Pro Glu<br>165                   170                   175                180 | 585 |
| gtg gcg ccc aag atc gcc gcg tgg gcc aag cgc tgc ggc gag cgg gag<br>Val Ala Pro Lys Ile Ala Ala Trp Ala Lys Arg Cys Gly Glu Arg Glu<br>                   185                   190                   195 | 633 |
| agc gtc gcc aag agc ctc tac tcg ccg gac aag gtg tac gac ttc atc<br>Ser Val Ala Lys Ser Leu Tyr Ser Pro Asp Lys Val Tyr Asp Phe Ile<br>            200                     205                     210 | 681 |
| ggc ctg ctc aag aag aag tac ggc atc gag taggcgcgcc gacggacgga<br>Gly Leu Leu Lys Lys Lys Tyr Gly Ile Glu<br>               215                   220 | 731 |
| cggacgggcc atgcaggcga cagccggccc gccgtccgga gggaagcaac aaataaatca | 791 |
| gggagcgatt tgggtggcct acaatgcgta cgtctggata gagtatttct ttctttcttt | 851 |
| cttcgtggaa taaagtgctc cgtgtgtgtg tggttggtgg ttgttggttg gatcagtcag | 911 |
| tgtgtgtggg tgcgtgttgt gtactcagta ctcgtgatgt gtgtgtgtgt caatgtgtca | 971 |
| accctggtct tcggtggggg cagcaccgag ttgccacctg ccattccatt tccattccgg | 1031 |
| gcgatgaata aattaaaaaa gagtctcatt tgtttaaaaa aaaaaaaaaa aaaa | 1085 |

<210> SEQ ID NO 2
<211> LENGTH: 222
<212> TYPE: PRT
<213> ORGANISM: Triticum aestivum L.

<400> SEQUENCE: 2

Met Ala Gly Glu Lys Gly Leu Val Leu Leu Asp Phe Trp Val Ser Pro
1               5                    10                   15

Phe Gly Gln Arg Val Arg Ile Ala Leu Ala Glu Lys Gly Leu Pro Tyr
               20                    25                   30

Glu Tyr Ala Glu Glu Asp Leu Met Ala Gly Lys Ser Asp Arg Leu Leu

```
                35                  40                  45
Arg Ala Asn Pro Val His Lys Lys Ile Pro Val Leu Leu His Asp Gly
 50                  55                  60
Arg Ala Val Asn Glu Ser Leu Ile Ile Leu Gln Tyr Leu Glu Glu Ala
 65                  70                  75                  80
Phe Pro Asp Ala Pro Ala Leu Leu Pro Ser Asp Pro Tyr Ala Arg Ala
                 85                  90                  95
Gln Ala Arg Phe Trp Ala Asp Tyr Val Asp Lys Lys Val Tyr Asp Cys
                100                 105                 110
Gly Ser Arg Leu Trp Lys Leu Lys Gly Glu Pro Gln Ala Gln Ala Arg
                115                 120                 125
Ala Glu Met Leu Asp Ile Leu Lys Thr Leu Asp Gly Ala Leu Gly Asp
130                 135                 140
Lys Pro Phe Phe Gly Gly Asp Lys Phe Gly Phe Val Asp Ala Ala Phe
145                 150                 155                 160
Ala Pro Phe Thr Ala Trp Phe His Ser Tyr Glu Arg Tyr Gly Glu Phe
                165                 170                 175
Ser Leu Pro Glu Val Ala Pro Lys Ile Ala Ala Trp Ala Lys Arg Cys
                180                 185                 190
Gly Glu Arg Glu Ser Val Ala Lys Ser Leu Tyr Ser Pro Asp Lys Val
                195                 200                 205
Tyr Asp Phe Ile Gly Leu Leu Lys Lys Lys Tyr Gly Ile Glu
                210                 215                 220

<210> SEQ ID NO 3
<211> LENGTH: 865
<212> TYPE: DNA
<213> ORGANISM: Triticum aestivum L.
<220> FEATURE:
<221> NAME/KEY: CDS
<222> LOCATION: (54)...(725)
<223> OTHER INFORMATION: WIC 1

<400> SEQUENCE: 3
ggaactcaac cattgatctt caagaagcgg aagcaaacag agcaaaaggt gtg atg      56
                                                          Met
                                                           1
gcg gcg ccg gcg gtg aag gtg tac ggg tgg gcg atg tcg ccg ttc gtg    104
Ala Ala Pro Ala Val Lys Val Tyr Gly Trp Ala Met Ser Pro Phe Val
          5                  10                  15
gcg cgc gcg ctg ctg tgc ctg gag gag gcc ggc gtg gag tac gag ctc    152
Ala Arg Ala Leu Leu Cys Leu Glu Glu Ala Gly Val Glu Tyr Glu Leu
             20                  25                  30
gtc ccc atg agc cgc gag gcc ggc gac cac cgc cag ccc gac ttc ctc    200
Val Pro Met Ser Arg Glu Ala Gly Asp His Arg Gln Pro Asp Phe Leu
 35                  40                  45
gcc cgg aac ccc ttc ggc cag gtc ccc gtt ctc gag gac ggc gac ctc    248
Ala Arg Asn Pro Phe Gly Gln Val Pro Val Leu Glu Asp Gly Asp Leu
 50                  55                  60                  65
acc atc ttc gag tcg cgc gcc gtc gcg agg cac gtg ctg cgc aag cac    296
Thr Ile Phe Glu Ser Arg Ala Val Ala Arg His Val Leu Arg Lys His
                 70                  75                  80
aaa ccg gag ctg ctg ggc tcc ggc tcg ccg gag tcg gcg gcg atg gtg    344
Lys Pro Glu Leu Leu Gly Ser Gly Ser Pro Glu Ser Ala Ala Met Val
             85                  90                  95
gac gtg tgg ctg gag gtg gag gcc cac cag cac cag acc ccg gcg ggc    392
Asp Val Trp Leu Glu Val Glu Ala His Gln His Gln Thr Pro Ala Gly
            100                 105                 110
```

```
acc atc gtc atg cag tgc atc ctc acc ccg ttc ctc ggc tgc cag cgc      440
Thr Ile Val Met Gln Cys Ile Leu Thr Pro Phe Leu Gly Cys Gln Arg
    115                 120                 125 gac cag gcc gcc atc gac gag aac gcg gca aag ctg acg aat ctg ttc      488
Asp Gln Ala Ala Ile Asp Glu Asn Ala Ala Lys Leu Thr Asn Leu Phe
130                 135                 140                 145 gac gtg tac gag gcg cgc ctg tcg gcg tcg agg tac ctt gcc ggg gag      536
Asp Val Tyr Glu Ala Arg Leu Ser Ala Ser Arg Tyr Leu Ala Gly Glu
                150                 155                 160 gcg gtc agc ctc gcg gac ctc agc cac ttc ccg ttc atg cga tac ttc      584
Ala Val Ser Leu Ala Asp Leu Ser His Phe Pro Phe Met Arg Tyr Phe
            165                 170                 175 atg gac acc gag tac gcg tcg ctg gtg gag gag cgc ccg cac gtg aag      632
Met Asp Thr Glu Tyr Ala Ser Leu Val Glu Glu Arg Pro His Val Lys
        180                 185                 190 gcg tgg tgg gag gag ttc aag gcc agc ccg gcg gcg aag agg gtg acg      680
Ala Trp Trp Glu Glu Phe Lys Ala Ser Pro Ala Ala Lys Arg Val Thr
    195                 200                 205 gag ttc atg ccg cca aac ttc ggg ttc gga aag aag gca gag aag          725
Glu Phe Met Pro Pro Asn Phe Gly Phe Gly Lys Lys Ala Glu Lys
210                 215                 220 tgatgacaag aacgaacacc gagcgaacat gttgtgtggt ctgtgcgacc cgaccatggc    785
tcaatgtttt gggctgtttg tgtttcacgc atgaatgaat aaaacaaaat gcttttgggt    845
ttcaaaaaaa aaaaaaaaaa                                                865

<210> SEQ ID NO 4
<211> LENGTH: 224
<212> TYPE: PRT
<213> ORGANISM: Triticum aestivum L.

<400> SEQUENCE: 4

Met Ala Ala Pro Ala Val Lys Val Tyr Gly Trp Ala Met Ser Pro Phe
1               5                   10                  15

Val Ala Arg Ala Leu Leu Cys Leu Glu Glu Ala Gly Val Glu Tyr Glu
            20                  25                  30

Leu Val Pro Met Ser Arg Glu Ala Gly Asp His Arg Gln Pro Asp Phe
        35                  40                  45

Leu Ala Arg Asn Pro Phe Gly Gln Val Pro Val Leu Glu Asp Gly Asp
    50                  55                  60

Leu Thr Ile Phe Glu Ser Arg Ala Val Ala Arg His Val Leu Arg Lys
65                  70                  75                  80

His Lys Pro Glu Leu Leu Gly Ser Gly Ser Pro Glu Ser Ala Ala Met
                85                  90                  95

Val Asp Val Trp Leu Glu Val Glu Ala His Gln His Gln Thr Pro Ala
            100                 105                 110

Gly Thr Ile Val Met Gln Cys Ile Leu Thr Pro Phe Leu Gly Cys Gln
        115                 120                 125

Arg Asp Gln Ala Ala Ile Asp Glu Asn Ala Ala Lys Leu Thr Asn Leu
    130                 135                 140

Phe Asp Val Tyr Glu Ala Arg Leu Ser Ala Ser Arg Tyr Leu Ala Gly
145                 150                 155                 160

Glu Ala Val Ser Leu Ala Asp Leu Ser His Phe Pro Phe Met Arg Tyr
                165                 170                 175

Phe Met Asp Thr Glu Tyr Ala Ser Leu Val Glu Glu Arg Pro His Val
            180                 185                 190

Lys Ala Trp Trp Glu Glu Phe Lys Ala Ser Pro Ala Ala Lys Arg Val
```

```
            195                 200                 205
Thr Glu Phe Met Pro Pro Asn Phe Gly Phe Gly Lys Lys Ala Glu Lys
        210                 215                 220

<210> SEQ ID NO 5
<211> LENGTH: 930
<212> TYPE: DNA
<213> ORGANISM: Triticum aestivum L.
<220> FEATURE:
<221> NAME/KEY: CDS
<222> LOCATION: (60)...(725)
<223> OTHER INFORMATION: WIC 2

<400> SEQUENCE: 5
cacgcgtcca tctccaagaa gcggaagcta gtggagcaga gcaaaccaag caaggttgg       59 atg gcg ccg gcg gtg aag gtg tac ggg tgg gcc gtg tcg ccg ttc gtg      107
Met Ala Pro Ala Val Lys Val Tyr Gly Trp Ala Val Ser Pro Phe Val
  1               5                  10                  15 gcg cgc cca ctg ctg tgc ctg gag gag gcc ggc gtc gag tac gag ctc      155
Ala Arg Pro Leu Leu Cys Leu Glu Glu Ala Gly Val Glu Tyr Glu Leu
             20                  25                  30 gtg tcc atg agc cgc gcg gcc ggc gac cac cgc cag ccg gac ttc ctc      203
Val Ser Met Ser Arg Ala Ala Gly Asp His Arg Gln Pro Asp Phe Leu
         35                  40                  45 gcc cgg aac ccc ttc ggc cag gtc ccc gtc ctc gag gac ggc gac ctc      251
Ala Arg Asn Pro Phe Gly Gln Val Pro Val Leu Glu Asp Gly Asp Leu
     50                  55                  60 acc ctc ttc gag tcg cgc gcg atc gcg agg cac gtg ctc cgg aag cac      299
Thr Leu Phe Glu Ser Arg Ala Ile Ala Arg His Val Leu Arg Lys His
 65                  70                  75                  80 aag ccg gag ctg ctg ggc tgc ggc tcg ccg gag gcg gag gcg atg gtg      347
Lys Pro Glu Leu Leu Gly Cys Gly Ser Pro Glu Ala Glu Ala Met Val
                 85                  90                  95 gac gtg tgg ctg gag gtg gag gcc cac cag tac aac ccc gcg gcc agc      395
Asp Val Trp Leu Glu Val Glu Ala His Gln Tyr Asn Pro Ala Ala Ser
            100                 105                 110 gcc atc gtg gtg cag tgc atc atc ttg ccg cta ctg ggc ggc gcg cgg      443
Ala Ile Val Val Gln Cys Ile Ile Leu Pro Leu Leu Gly Gly Ala Arg
        115                 120                 125 gac cag gcg gtg gtg gac gag aac gta gcc aag ctc aag aag gtg ctg      491
Asp Gln Ala Val Val Asp Glu Asn Val Ala Lys Leu Lys Lys Val Leu
    130                 135                 140 gag gtg tac gag gca cgg ctg tcg gcg tcc agg tac ctc gcc ggg gac      539
Glu Val Tyr Glu Ala Arg Leu Ser Ala Ser Arg Tyr Leu Ala Gly Asp
145                 150                 155                 160 gac atc agc ctc gcc gac ctc agc cac ttc ccc ttc acg cgc tac ttc      587
Asp Ile Ser Leu Ala Asp Leu Ser His Phe Pro Phe Thr Arg Tyr Phe
                165                 170                 175 atg gag acg gag tac gcg ccg ctg gtg gcg gag ctc ccc cac gtg aac      635
Met Glu Thr Glu Tyr Ala Pro Leu Val Ala Glu Leu Pro His Val Asn
            180                 185                 190 gcg tgg tgg gag ggg ctc aag gcc agg ccg gcc gcg agg aag gtg acg      683
Ala Trp Trp Glu Gly Leu Lys Ala Arg Pro Ala Ala Arg Lys Val Thr
        195                 200                 205 gag ctc atg ccg ccg gac ctt ggg ctt gga aag aaa gca gag                725
Glu Leu Met Pro Pro Asp Leu Gly Leu Gly Lys Lys Ala Glu
    210                 215                 220 tagtgatgac tgccgccaac gttcaccagg atcgagcaag tcactgtcga gtctccggtt      785
ttgcgttgta cggcaccggg gcaccggcct atatttttctg taccagtggc tcgtgttttg      845
```

```
atgttttagt ctcacgcttg aataaaatgc aagatatacc catcggttct aaaagaaaaa    905
aaaaaaaaaa aaaaaaaaaa aaaaa                                           930
```

<210> SEQ ID NO 6
<211> LENGTH: 222
<212> TYPE: PRT
<213> ORGANISM: Triticum aestivum L.

<400> SEQUENCE: 6

```
Met Ala Pro Ala Val Lys Val Tyr Gly Trp Ala Val Ser Pro Phe Val
 1               5                   10                  15

Ala Arg Pro Leu Leu Cys Leu Glu Glu Ala Gly Val Glu Tyr Glu Leu
                20                  25                  30

Val Ser Met Ser Arg Ala Ala Gly Asp His Arg Gln Pro Asp Phe Leu
            35                  40                  45

Ala Arg Asn Pro Phe Gly Gln Val Pro Val Leu Glu Asp Gly Asp Leu
        50                  55                  60

Thr Leu Phe Glu Ser Arg Ala Ile Ala Arg His Val Leu Arg Lys His
 65                  70                  75                  80

Lys Pro Glu Leu Leu Gly Cys Gly Ser Pro Glu Ala Glu Ala Met Val
                85                  90                  95

Asp Val Trp Leu Glu Val Glu Ala His Gln Tyr Asn Pro Ala Ala Ser
            100                 105                 110

Ala Ile Val Val Gln Cys Ile Ile Leu Pro Leu Leu Gly Gly Ala Arg
        115                 120                 125

Asp Gln Ala Val Val Asp Glu Asn Val Ala Lys Leu Lys Lys Val Leu
    130                 135                 140

Glu Val Tyr Glu Ala Arg Leu Ser Ala Ser Arg Tyr Leu Ala Gly Asp
145                 150                 155                 160

Asp Ile Ser Leu Ala Asp Leu Ser His Phe Pro Phe Thr Arg Tyr Phe
                165                 170                 175

Met Glu Thr Glu Tyr Ala Pro Leu Val Ala Glu Leu Pro His Val Asn
            180                 185                 190

Ala Trp Trp Glu Gly Leu Lys Ala Arg Pro Ala Ala Arg Lys Val Thr
        195                 200                 205

Glu Leu Met Pro Pro Asp Leu Gly Leu Gly Lys Lys Ala Glu
    210                 215                 220
```

<210> SEQ ID NO 7
<211> LENGTH: 927
<212> TYPE: DNA
<213> ORGANISM: Triticum aestivum L.
<220> FEATURE:
<221> NAME/KEY: CDS
<222> LOCATION: (72)...(707)
<223> OTHER INFORMATION: WIC 3, WIC 7, and WIC 8

<400> SEQUENCE: 7

```
agcggcttta cctaccgaga agaagagaga aaaaaggttc gagtgcgttc cagagtgagg    60
agtgagaaga g atg gct ccg gtg aag ctg tac ggc gcg acc ctg tcg tgg   110
            Met Ala Pro Val Lys Leu Tyr Gly Ala Thr Leu Ser Trp
              1               5                   10 aac gtc acc agg tgc gtg gcg gcg ctg gag gag gcc ggc gtc cag tac   158
Asn Val Thr Arg Cys Val Ala Ala Leu Glu Glu Ala Gly Val Gln Tyr
             15                  20                  25 gag atc gta ccc atc aac ttc ggc acc ggc gag cac aag agc ccc gac   206
Glu Ile Val Pro Ile Asn Phe Gly Thr Gly Glu His Lys Ser Pro Asp
         30                  35                  40                  45
```

```
cac ctc gcc agg aac ccc ttc ggc cag gtg cca gct ttg cag gat ggt    254
His Leu Ala Arg Asn Pro Phe Gly Gln Val Pro Ala Leu Gln Asp Gly
                50                  55                  60 gac tta tac gtc ttc gaa tca cgt gct att tgc aag tac gcg tgc cgc    302
Asp Leu Tyr Val Phe Glu Ser Arg Ala Ile Cys Lys Tyr Ala Cys Arg
            65                  70                  75 aag aac aag cca gag ctg ttg aag gag ggc gac atc aag gag tca gca    350
Lys Asn Lys Pro Glu Leu Leu Lys Glu Gly Asp Ile Lys Glu Ser Ala
        80                  85                  90 atg gtg gat gtg tgg ctc gag gtg gag gcc cat cag tac act gcc gct    398
Met Val Asp Val Trp Leu Glu Val Glu Ala His Gln Tyr Thr Ala Ala
    95                 100                 105 ctg agc ccc att ctc ttc gag tgc ctt atc cat cca atg ctt ggg gga    446
Leu Ser Pro Ile Leu Phe Glu Cys Leu Ile His Pro Met Leu Gly Gly
110                 115                 120                 125 gcc act gac cag aag gtc atc gac gac aac ctt gtt aag atc aag aac    494
Ala Thr Asp Gln Lys Val Ile Asp Asp Asn Leu Val Lys Ile Lys Asn
            130                 135                 140 gtg ctg gcg gtg tac gag gcg cac ctg agc aag tcc aag tac ctg gct    542
Val Leu Ala Val Tyr Glu Ala His Leu Ser Lys Ser Lys Tyr Leu Ala
        145                 150                 155 gga gac ttc ctc agt ctt gcg gac ctt aac cat gtg tct gtc acc ctg    590
Gly Asp Phe Leu Ser Leu Ala Asp Leu Asn His Val Ser Val Thr Leu
    160                 165                 170 tgc ttg gcg gct aca ccc tat gcg tct ctg ttc gac gcg tac ccg cat    638
Cys Leu Ala Ala Thr Pro Tyr Ala Ser Leu Phe Asp Ala Tyr Pro His
175                 180                 185 gtg aag gcc tgg tgg act gac ctg ctg gcg agg ccg tcc gtc cag aag    686
Val Lys Ala Trp Trp Thr Asp Leu Leu Ala Arg Pro Ser Val Gln Lys
190                 195                 200                 205 gtc gca gcg ctg atg aag cca tgatcttaat tgctggtgct cgttcgtcgc       737
Val Ala Ala Leu Met Lys Pro
                210 gaaataagcc gaggtgtgtg cccccgatg tgtgcctgta cgagtgtgtg ttcttgtgat   797 gtctcctcgt gttgaatgtt caggcttgtg cttgcgatcc tgtctcatct tttactgaaa  857 tgagcgttcc tatgctctgg tttaataata aattgtgcct agatattatc tcaaaaaaaa  917 aaaaaaaaaa                                                        927

<210> SEQ ID NO 8
<211> LENGTH: 212
<212> TYPE: PRT
<213> ORGANISM: Triticum aestivum L.

<400> SEQUENCE: 8

Met Ala Pro Val Lys Leu Tyr Gly Ala Thr Leu Ser Trp Asn Val Thr
  1               5                  10                  15

Arg Cys Val Ala Ala Leu Glu Glu Ala Gly Val Gln Tyr Glu Ile Val
                 20                  25                  30

Pro Ile Asn Phe Gly Thr Gly Glu His Lys Ser Pro Asp His Leu Ala
             35                  40                  45

Arg Asn Pro Phe Gly Gln Val Pro Ala Leu Gln Asp Gly Asp Leu Tyr
         50                  55                  60

Val Phe Glu Ser Arg Ala Ile Cys Lys Tyr Ala Cys Arg Lys Asn Lys
 65                  70                  75                  80

Pro Glu Leu Leu Lys Glu Gly Asp Ile Lys Glu Ser Ala Met Val Asp
                 85                  90                  95
```

```
Val Trp Leu Glu Val Glu Ala His Gln Tyr Thr Ala Ala Leu Ser Pro
            100                 105                 110

Ile Leu Phe Glu Cys Leu Ile His Pro Met Leu Gly Gly Ala Thr Asp
            115                 120                 125

Gln Lys Val Ile Asp Asp Asn Leu Val Lys Ile Lys Asn Val Leu Ala
130                 135                 140

Val Tyr Glu Ala His Leu Ser Lys Ser Lys Tyr Leu Ala Gly Asp Phe
145                 150                 155                 160

Leu Ser Leu Ala Asp Leu Asn His Val Ser Val Thr Leu Cys Leu Ala
                165                 170                 175

Ala Thr Pro Tyr Ala Ser Leu Phe Asp Ala Tyr Pro His Val Lys Ala
            180                 185                 190

Trp Trp Thr Asp Leu Leu Ala Arg Pro Ser Val Gln Lys Val Ala Ala
            195                 200                 205

Leu Met Lys Pro
        210

EQ ID NO 9
ENGTH: 866
YPE: DNA
RGANISM: Triticum aestivum L.
EATURE:
AME/KEY: CDS
OCATION: (45)...(683)
THER INFORMATION: WIC 5

EQUENCE: 9 gaagcaggca acaggcgagc aggaaggaag caagagaggt ggag atg gcg ccc atc      56
                                                  Met Ala Pro Ile
                                                    1 aag ctg tac ggg atg atg ctg tcg gcc aac gtg acc cgc gtg acc acg     104
Lys Leu Tyr Gly Met Met Leu Ser Ala Asn Val Thr Arg Val Thr Thr
  5                  10                  15                  20 ctg ctc aac gag ctc ggc ctc gag ttc gac ttc gtc gac gtc gac ctc     152
Leu Leu Asn Glu Leu Gly Leu Glu Phe Asp Phe Val Asp Val Asp Leu
                 25                  30                  35 cgc acc ggc gcc cac aag cac ccc gac ttc ctc aag ctc aac cct ttc     200
Arg Thr Gly Ala His Lys His Pro Asp Phe Leu Lys Leu Asn Pro Phe
             40                  45                  50 ggc cag atc ccc gcg ctg cag gac gga gac gaa gtt gtc ttc gag tcg     248
Gly Gln Ile Pro Ala Leu Gln Asp Gly Asp Glu Val Val Phe Glu Ser
         55                  60                  65 cgc gcc atc aac cgg tac atc gcg acc aag tac ggg gcg tcc ctg ctg     296
Arg Ala Ile Asn Arg Tyr Ile Ala Thr Lys Tyr Gly Ala Ser Leu Leu
     70                  75                  80 ccg acg ccg tcg gcc aag ctg gag gcg tgg ctg gag gtg gag tcg cac     344
Pro Thr Pro Ser Ala Lys Leu Glu Ala Trp Leu Glu Val Glu Ser His
 85                  90                  95                 100 cac ttc tac ccg ccg gcg cgg acg ctg gtg tac gag ctg gtc atc aag     392
His Phe Tyr Pro Pro Ala Arg Thr Leu Val Tyr Glu Leu Val Ile Lys
                105                 110                 115 ccc atg ctg ggc gcc ccc acc gac gcc gcc gag gtg gac aag aac gcc     440
Pro Met Leu Gly Ala Pro Thr Asp Ala Ala Glu Val Asp Lys Asn Ala
            120                 125                 130 gcc gac ctc gcc aag ctg ctc gac gtc tac gag gcc cac ctc gcc gcc     488
Ala Asp Leu Ala Lys Leu Leu Asp Val Tyr Glu Ala His Leu Ala Ala
        135                 140                 145 ggg aac aag tac ctg gcc ggc gac gcc ttc ccg ctc gcc gac gcc aac     536
Gly Asn Lys Tyr Leu Ala Gly Asp Ala Phe Pro Leu Ala Asp Ala Asn
    150                 155                 160
```

```
cac atg tcc tac ctc ttc atg ctc acc aag agc ccc aag gcg gac ctg      584
His Met Ser Tyr Leu Phe Met Leu Thr Lys Ser Pro Lys Ala Asp Leu
165             170                 175                 180 gtg gcc tcc cgc ccg cac gtc aag gcc tgg tgg gag gag atc tcc gcc      632
Val Ala Ser Arg Pro His Val Lys Ala Trp Trp Glu Glu Ile Ser Ala
            185                 190                 195 cgc ccc gcc tgg gcc aag acc gtc gcc tcc atc ccc ctc ccg ccc gcc      680
Arg Pro Ala Trp Ala Lys Thr Val Ala Ser Ile Pro Leu Pro Pro Ala
        200                 205                 210 gtc tgaggttgct tgtttggctg cggcgagaac ggaataaaat cgcgatgatg           733
Val gaataaacaa cttttagag aggaagcttg gaattcttgg tgttgctgct gttgaatgtt     793
gaatcttggt gttgaatgtt tacggcacat ctaatttatc cagttttttt ggcgtgaaaa   853
aaaaaaaaaa aaa                                                       866

<210> SEQ ID NO 10
<211> LENGTH: 213
<212> TYPE: PRT
<213> ORGANISM: Triticum aestivum L.

<400> SEQUENCE: 10

Met Ala Pro Ile Lys Leu Tyr Gly Met Met Leu Ser Ala Asn Val Thr
1               5                   10                  15

Arg Val Thr Thr Leu Leu Asn Glu Leu Gly Leu Glu Phe Asp Phe Val
            20                  25                  30

Asp Val Asp Leu Arg Thr Gly Ala His Lys His Pro Asp Phe Leu Lys
        35                  40                  45

Leu Asn Pro Phe Gly Gln Ile Pro Ala Leu Gln Asp Gly Asp Glu Val
    50                  55                  60

Val Phe Glu Ser Arg Ala Ile Asn Arg Tyr Ile Ala Thr Lys Tyr Gly
65                  70                  75                  80

Ala Ser Leu Leu Pro Thr Pro Ser Ala Lys Leu Glu Ala Trp Leu Glu
                85                  90                  95

Val Glu Ser His His Phe Tyr Pro Pro Ala Arg Thr Leu Val Tyr Glu
            100                 105                 110

Leu Val Ile Lys Pro Met Leu Gly Ala Pro Thr Asp Ala Ala Glu Val
        115                 120                 125

Asp Lys Asn Ala Ala Asp Leu Ala Lys Leu Leu Asp Val Tyr Glu Ala
    130                 135                 140

His Leu Ala Ala Gly Asn Lys Tyr Leu Ala Gly Asp Ala Phe Pro Leu
145                 150                 155                 160

Ala Asp Ala Asn His Met Ser Tyr Leu Phe Met Leu Thr Lys Ser Pro
                165                 170                 175

Lys Ala Asp Leu Val Ala Ser Arg Pro His Val Lys Ala Trp Trp Glu
            180                 185                 190

Glu Ile Ser Ala Arg Pro Ala Trp Ala Lys Thr Val Ala Ser Ile Pro
        195                 200                 205

Leu Pro Pro Ala Val
    210

<210> SEQ ID NO 11
<211> LENGTH: 897
<212> TYPE: DNA
<213> ORGANISM: Triticum aestivum L.
<220> FEATURE:
<221> NAME/KEY: CDS
```

<222> LOCATION: (15)...(668)
<223> OTHER INFORMATION: WIC 4 and WIC 10
<221> NAME/KEY: gene
<222> LOCATION: (1)...(897)
<223> OTHER INFORMATION: WIC 4 cDNA

<400> SEQUENCE: 11

```
aaccaaggga aaca atg gcg ccg gtg aag gtg ttc ggg ccg gcg atg tcg         50
              Met Ala Pro Val Lys Val Phe Gly Pro Ala Met Ser
              1               5                  10 acc aac gtg gcc cgg gtg ctg gtg tgc ctg gag gag gtc ggc gcc gag         98
Thr Asn Val Ala Arg Val Leu Val Cys Leu Glu Glu Val Gly Ala Glu
        15                  20                  25 tac gag gtg gtc gac atc gat ttc aag gcc atg gag cac aag agc ccc        146
Tyr Glu Val Val Asp Ile Asp Phe Lys Ala Met Glu His Lys Ser Pro
    30                  35                  40 gag cat ctc gtc aga aac ccg ttc ggc caa atc cct gcc ttc cag gat        194
Glu His Leu Val Arg Asn Pro Phe Gly Gln Ile Pro Ala Phe Gln Asp
45                  50                  55                  60 ggg gat ctg ctt ctc ttc gag tca cgc gca att gcg agg tac gtg ctc        242
Gly Asp Leu Leu Leu Phe Glu Ser Arg Ala Ile Ala Arg Tyr Val Leu
                65                  70                  75 cgc aag tac aag aag aac gaa gtg gac ctg ctg agg gaa ggc gac ctc        290
Arg Lys Tyr Lys Lys Asn Glu Val Asp Leu Leu Arg Glu Gly Asp Leu
            80                  85                  90 aag gag gcg gcg atg gtg gac gta tgg acg gag gtg gac gcg cac acc        338
Lys Glu Ala Ala Met Val Asp Val Trp Thr Glu Val Asp Ala His Thr
        95                  100                 105 tac aac ccg gcc atc tcg ccg atc gtg tac gag tgc tca tca acc gct        386
Tyr Asn Pro Ala Ile Ser Pro Ile Val Tyr Glu Cys Ser Ser Thr Ala
    110                 115                 120 cat gcg cgg ctg ccg acc aac caa acg gtg gtg gac gag agc ctg gag        434
His Ala Arg Leu Pro Thr Asn Gln Thr Val Val Asp Glu Ser Leu Glu
125                 130                 135                 140 aag ctc aag aac gtg ctg gag gtc tac gag gcg cgc ctg tcc aag cac        482
Lys Leu Lys Asn Val Leu Glu Val Tyr Glu Ala Arg Leu Ser Lys His
                145                 150                 155 gac tac ctc gcc ggg gac ttc gtc agc ttc gcg gac ctc aac cac ttc        530
Asp Tyr Leu Ala Gly Asp Phe Val Ser Phe Ala Asp Leu Asn His Phe
            160                 165                 170 ccc tac acc ttc tac ttc atg gcc acg ccg cac gcg gcc ctc ttc gac        578
Pro Tyr Thr Phe Tyr Phe Met Ala Thr Pro His Ala Ala Leu Phe Asp
        175                 180                 185 tcg tac ccg cac gtc aag gcc tgg tgg gag agg atc atg gcg agg ccg        626
Ser Tyr Pro His Val Lys Ala Trp Trp Glu Arg Ile Met Ala Arg Pro
    190                 195                 200 gcc gtg aag aag ctc gcc gcg cag atg gtt ccc aag aag ccg                668
Ala Val Lys Lys Leu Ala Ala Gln Met Val Pro Lys Lys Pro
205                 210                 215 tgatttgcta ggcgggatct cgcatcgtgg gatccgattc cgatcactga tctgtgtggc       728
gttttctttt cttgttggtg tcgcgaataa ggcaaatgag ctcgtgtgtg tgtggctgga       788
attgcaccag cgtgcagttt ttgcgctttg cgtgtgtgtg gtcgtgaaaa ctcttgagat       848
ggaacaatgt cttcgtaatg ctttcacatt ttaaaaaaaa aaaaaaaaa                   897
```

<210> SEQ ID NO 12
<211> LENGTH: 218
<212> TYPE: PRT
<213> ORGANISM: Triticum aestivum L.

<400> SEQUENCE: 12

```
Met Ala Pro Val Lys Val Phe Gly Pro Ala Met Ser Thr Asn Val Ala
 1               5                  10                  15

Arg Val Leu Val Cys Leu Glu Glu Val Gly Ala Glu Tyr Glu Val Val
                20                  25                  30

Asp Ile Asp Phe Lys Ala Met Glu His Lys Ser Pro Glu His Leu Val
            35                  40                  45

Arg Asn Pro Phe Gly Gln Ile Pro Ala Phe Gln Asp Gly Asp Leu Leu
        50                  55                  60

Leu Phe Glu Ser Arg Ala Ile Ala Arg Tyr Val Leu Arg Lys Tyr Lys
 65                  70                  75                  80

Lys Asn Glu Val Asp Leu Leu Arg Glu Gly Asp Leu Lys Glu Ala Ala
                85                  90                  95

Met Val Asp Val Trp Thr Glu Val Asp Ala His Thr Tyr Asn Pro Ala
                100                 105                 110

Ile Ser Pro Ile Val Tyr Glu Cys Ser Ser Thr Ala His Ala Arg Leu
            115                 120                 125

Pro Thr Asn Gln Thr Val Val Asp Glu Ser Leu Glu Lys Leu Lys Asn
        130                 135                 140

Val Leu Glu Val Tyr Glu Ala Arg Leu Ser Lys His Asp Tyr Leu Ala
145                 150                 155                 160

Gly Asp Phe Val Ser Phe Ala Asp Leu Asn His Phe Pro Tyr Thr Phe
                165                 170                 175

Tyr Phe Met Ala Thr Pro His Ala Ala Leu Phe Asp Ser Tyr Pro His
                180                 185                 190

Val Lys Ala Trp Trp Glu Arg Ile Met Ala Arg Pro Ala Val Lys Lys
                195                 200                 205

Leu Ala Ala Gln Met Val Pro Lys Lys Pro
        210                 215
```

EQ ID NO 13
ENGTH: 721
YPE: DNA
RGANISM: Triticum aestivum L.
EATURE:
AME/KEY: CDS
OCATION: (21)...(686)
THER INFORMATION: Glutathione S transferase
AME/KEY: gene
OCATION: (1)...(721)
THER INFORMATION: TA 27 cDNA

EQUENCE: 13

```
ttcggcacga ggaagaaggg atg gag cct atg aag gtg tac ggc tgg gcg gtg        53
                     Met Glu Pro Met Lys Val Tyr Gly Trp Ala Val
                      1               5                  10 tcg cca tgg atg gcg cgg gtc ctc gtc tcc ctg gag gag gcc ggc gcc        101
Ser Pro Trp Met Ala Arg Val Leu Val Ser Leu Glu Glu Ala Gly Ala
                15                  20                  25 gac tac gag ctc gtg ccc atg agc cgc aac ggc ggc gac cac cgg cgg        149
Asp Tyr Glu Leu Val Pro Met Ser Arg Asn Gly Gly Asp His Arg Arg
            30                  35                  40 ccg gag cac ctc gcc aga aac ccc ttc ggt gag atc ccg gtg ctc gaa        197
Pro Glu His Leu Ala Arg Asn Pro Phe Gly Glu Ile Pro Val Leu Glu
        45                  50                  55 tac ggc ggt ctg acg ctt tac caa tcc cgc gcc att gca agg cat att        245
Tyr Gly Gly Leu Thr Leu Tyr Gln Ser Arg Ala Ile Ala Arg His Ile
 60                  65                  70                  75 ctc cgc aaa cac aag ccc ggg ctt cta gga gca ggc agc ctc gag gag        293
```

```
                                                                    -continued Leu Arg Lys His Lys Pro Gly Leu Leu Gly Ala Gly Ser Leu Glu Glu
                    80                  85                  90 tcg gcg atg gtg gat gta tgg gtc gac gtg gat gcc cac cac ctg gag      341
Ser Ala Met Val Asp Val Trp Val Asp Val Asp Ala His His Leu Glu
                95                  100                 105 ccc gta ctc aag ccc atc gtg tgg aac tgc atc atc aac ccg ttc gtc      389
Pro Val Leu Lys Pro Ile Val Trp Asn Cys Ile Ile Asn Pro Phe Val
            110                 115                 120 ggg agg gac gtc gac cag ggc ctc gtc gat gag agc gtc gag aag ctc      437
Gly Arg Asp Val Asp Gln Gly Leu Val Asp Glu Ser Val Glu Lys Leu
        125                 130                 135 aag aag ctg ctg gag gtg tac gag gca aga ctg tca agc aac aag tac      485
Lys Lys Leu Leu Glu Val Tyr Glu Ala Arg Leu Ser Ser Asn Lys Tyr
140                 145                 150                 155 ttg gcc ggg gat ttc gtc agc ttc gcc gac ctc acc cat ttc tcc ttc      533
Leu Ala Gly Asp Phe Val Ser Phe Ala Asp Leu Thr His Phe Ser Phe
                160                 165                 170 atg cgc tac ttc atg gcg acg gag cat gcg gtt gtg ctc gat gcg tat      581
Met Arg Tyr Phe Met Ala Thr Glu His Ala Val Val Leu Asp Ala Tyr
            175                 180                 185 ccg cat gtg aag gca tgg tgg aag gcg ctg ctg gca agg cca tcg gtc      629
Pro His Val Lys Ala Trp Trp Lys Ala Leu Leu Ala Arg Pro Ser Val
        190                 195                 200 aag aag gtg ata gct ggc atg cct ccg gat ttt gga ttc ggg agc ggg      677
Lys Lys Val Ile Ala Gly Met Pro Pro Asp Phe Gly Phe Gly Ser Gly
205                 210                 215 aga ata cca tgataaagca tgcttgtttg tctatgatgc tctga                   721
Arg Ile Pro
220

<210> SEQ ID NO 14
<211> LENGTH: 222
<212> TYPE: PRT
<213> ORGANISM: Triticum aestivum L.

<400> SEQUENCE: 14

Met Glu Pro Met Lys Val Tyr Gly Trp Ala Val Ser Pro Trp Met Ala
1               5                   10                  15

Arg Val Leu Val Ser Leu Glu Glu Ala Gly Ala Asp Tyr Glu Leu Val
                20                  25                  30

Pro Met Ser Arg Asn Gly Gly Asp His Arg Arg Pro Glu His Leu Ala
            35                  40                  45

Arg Asn Pro Phe Gly Glu Ile Pro Val Leu Glu Tyr Gly Gly Leu Thr
        50                  55                  60

Leu Tyr Gln Ser Arg Ala Ile Ala Arg His Ile Leu Arg Lys His Lys
65                  70                  75                  80

Pro Gly Leu Leu Gly Ala Gly Ser Leu Glu Glu Ser Ala Met Val Asp
                85                  90                  95

Val Trp Val Asp Val Asp Ala His His Leu Glu Pro Val Leu Lys Pro
                100                 105                 110

Ile Val Trp Asn Cys Ile Ile Asn Pro Phe Val Gly Arg Asp Val Asp
            115                 120                 125

Gln Gly Leu Val Asp Glu Ser Val Glu Lys Leu Lys Lys Leu Leu Glu
        130                 135                 140

Val Tyr Glu Ala Arg Leu Ser Ser Asn Lys Tyr Leu Ala Gly Asp Phe
145                 150                 155                 160

Val Ser Phe Ala Asp Leu Thr His Phe Ser Phe Met Arg Tyr Phe Met
                165                 170                 175
```

```
Ala Thr Glu His Ala Val Val Leu Asp Ala Tyr Pro His Val Lys Ala
            180                 185                 190

Trp Trp Lys Ala Leu Leu Ala Arg Pro Ser Val Lys Lys Val Ile Ala
        195                 200                 205

Gly Met Pro Pro Asp Phe Gly Phe Gly Ser Gly Arg Ile Pro
    210                 215                 220

<210> SEQ ID NO 15
<211> LENGTH: 926
<212> TYPE: DNA
<213> ORGANISM: Triticum aestivum L.
<220> FEATURE:
<221> NAME/KEY: CDS
<222> LOCATION: (66)...(764)
<223> OTHER INFORMATION: Glutathione S transferase
<221> NAME/KEY: gene
<222> LOCATION: (1)...(926)
<223> OTHER INFORMATION: cDNA clone ICR

<400> SEQUENCE: 15
aaccactttc atcaacgtct cctacgctca ccgttcgttg ctccgcacat cagcaggact    60 tgcca atg gcg gga gac ggc gag ctg aag ctg ctg ggc gtg tgg acg agc   110
      Met Ala Gly Asp Gly Glu Leu Lys Leu Leu Gly Val Trp Thr Ser
       1               5                  10                  15 ccg ttc gtc atc agg gtg cgc gtg gtg ctc aac ctc aag tcg ctg ccg    158
Pro Phe Val Ile Arg Val Arg Val Val Leu Asn Leu Lys Ser Leu Pro
                 20                  25                  30 tac gag tac gtg gag gag agc ctg ggc agc aag agc gcg ctc ctc ctg    206
Tyr Glu Tyr Val Glu Glu Ser Leu Gly Ser Lys Ser Ala Leu Leu Leu
             35                  40                  45 ggc tcc aac ccg gtg cac cag agc gtg ccc gtc ctc ctc cac ggc ggc    254
Gly Ser Asn Pro Val His Gln Ser Val Pro Val Leu Leu His Gly Gly
         50                  55                  60 cgc ccc gtg aac gag tcc cag gtc atc gtg cag tac atc gac gag gtc    302
Arg Pro Val Asn Glu Ser Gln Val Ile Val Gln Tyr Ile Asp Glu Val
     65                  70                  75 tgg gcg ggg gcc ggc ccg tcc gtg ctc ccg gcc gac ccc tac gag cgc    350
Trp Ala Gly Ala Gly Pro Ser Val Leu Pro Ala Asp Pro Tyr Glu Arg
 80                  85                  90                  95 gcc acg gcg cgc ttc tgg gcg gcg tac gtc gac gac aag gtc ggg tcg    398
Ala Thr Ala Arg Phe Trp Ala Ala Tyr Val Asp Asp Lys Val Gly Ser
                100                 105                 110 gcg tgg acg ggg atg ctc ttc tcg tgc aag acg gag gag gag cgg gcg    446
Ala Trp Thr Gly Met Leu Phe Ser Cys Lys Thr Glu Glu Glu Arg Ala
            115                 120                 125 gag gcg gtg tcc cgg gcc gtg gcg gcg ctg gag acc ctg gag ggc gcg    494
Glu Ala Val Ser Arg Ala Val Ala Ala Leu Glu Thr Leu Glu Gly Ala
        130                 135                 140 ttc gcg gag tgc tcc aag ggg aag gcg ttc ttc ggc ggc gac gcc atc    542
Phe Ala Glu Cys Ser Lys Gly Lys Ala Phe Phe Gly Gly Asp Ala Ile
145                 150                 155 ggg ttc gtc gac gtc gtg ctt ggc ggc tac ctc ggc tgg ttc ggc gcg    590
Gly Phe Val Asp Val Val Leu Gly Gly Tyr Leu Gly Trp Phe Gly Ala
            160                 165                 170                 175 atc gac aag atc atc ggg cgc cgg ctg atc gac ccg gcg agg acg ccg    638
Ile Asp Lys Ile Ile Gly Arg Arg Leu Ile Asp Pro Ala Arg Thr Pro
                180                 185                 190 ctg ctg gcc agg tgg gag gag cgg ttc cgc gcg gcg gac gcg gcc aag    686
Leu Leu Ala Arg Trp Glu Glu Arg Phe Arg Ala Ala Asp Ala Ala Lys
            195                 200                 205
```

```
ggc gtc gtg ccg gac gac gcc gac aag atg ctc gag ttc ttg ccc acc    734
Gly Val Val Pro Asp Asp Ala Asp Lys Met Leu Glu Phe Leu Pro Thr
        210                 215                 220 gtg ctc gct tgg atc gcc ggc aaa gcg aag tgaactgtgt ctgtgaggcc      784
Val Leu Ala Trp Ile Ala Gly Lys Ala Lys
    225                 230 gtgacatcgc cagctcgtga catgtgtgtt tgtgtgtgtc tgagtccgtc cagtgtgtgc   844
tgaataaatg caccgcatgt cgtgtgttgt accaagggca aacaatgctg aataattttg   904
ctgttaaaaa aaaaaaaaaa aa                                            926

<210> SEQ ID NO 16
<211> LENGTH: 233
<212> TYPE: PRT
<213> ORGANISM: Triticum aestivum L.

<400> SEQUENCE: 16

Met Ala Gly Asp Gly Glu Leu Lys Leu Leu Gly Val Trp Thr Ser Pro
 1               5                  10                  15

Phe Val Ile Arg Val Arg Val Leu Asn Leu Lys Ser Leu Pro Tyr
            20                  25                  30

Glu Tyr Val Glu Glu Ser Leu Gly Ser Lys Ser Ala Leu Leu Leu Gly
        35                  40                  45

Ser Asn Pro Val His Gln Ser Val Pro Val Leu Leu His Gly Gly Arg
    50                  55                  60

Pro Val Asn Glu Ser Gln Val Ile Val Gln Tyr Ile Asp Glu Val Trp
65                  70                  75                  80

Ala Gly Ala Gly Pro Ser Val Leu Pro Ala Asp Pro Tyr Glu Arg Ala
                85                  90                  95

Thr Ala Arg Phe Trp Ala Ala Tyr Val Asp Asp Lys Val Gly Ser Ala
            100                 105                 110

Trp Thr Gly Met Leu Phe Ser Cys Lys Thr Glu Glu Arg Ala Glu
        115                 120                 125

Ala Val Ser Arg Ala Val Ala Ala Leu Glu Thr Leu Glu Gly Ala Phe
    130                 135                 140

Ala Glu Cys Ser Lys Gly Lys Ala Phe Phe Gly Gly Asp Ala Ile Gly
145                 150                 155                 160

Phe Val Asp Val Val Leu Gly Gly Tyr Leu Gly Trp Phe Gly Ala Ile
                165                 170                 175

Asp Lys Ile Ile Gly Arg Arg Leu Ile Asp Pro Ala Arg Thr Pro Leu
            180                 185                 190

Leu Ala Arg Trp Glu Glu Arg Phe Arg Ala Ala Asp Ala Ala Lys Gly
        195                 200                 205

Val Val Pro Asp Asp Ala Asp Lys Met Leu Glu Phe Leu Pro Thr Val
    210                 215                 220

Leu Ala Trp Ile Ala Gly Lys Ala Lys
225                 230

<210> SEQ ID NO 17
<211> LENGTH: 1043
<212> TYPE: DNA
<213> ORGANISM: Triticum aestivum L.
<220> FEATURE:
<221> NAME/KEY: CDS
<222> LOCATION: (39)...(767)
<223> OTHER INFORMATION: Glutathione S transferase
<221> NAME/KEY: gene
<222> LOCATION: (1)...(1043)
<223> OTHER INFORMATION: cDNA clones ICC, ICP, and ICV
```

<400> SEQUENCE: 17

```
aggacacgag tatcagggag gaagacgagg aaacgttg atg gcc ggc ggt gaa gag      56
                                          Met Ala Gly Gly Glu Glu
                                          1               5 ctg aag ctg ctg ggg tgg tgg gcg ccc ggg gtg agt ccc tac gtg ctg       104
Leu Lys Leu Leu Gly Trp Trp Ala Pro Gly Val Ser Pro Tyr Val Leu
        10                  15                  20 cgc gcc cag atg gcg ctc gcc gta aag ggg ctg agc tac gac tac ctc       152
Arg Ala Gln Met Ala Leu Ala Val Lys Gly Leu Ser Tyr Asp Tyr Leu
    25                  30                  35 ccc gag gac cgc tgg tcc acg agc gac ctc ctc atc gcg tcc aac ccc       200
Pro Glu Asp Arg Trp Ser Thr Ser Asp Leu Leu Ile Ala Ser Asn Pro
40                  45                  50 gtg tac aag aag gtg ccc gtc ctc att cac aac ggc agg ccc gtc tgc       248
Val Tyr Lys Lys Val Pro Val Leu Ile His Asn Gly Arg Pro Val Cys
55                  60                  65                  70 gag tcg ctg ctc atc ctg gag tac ctc gac gac gcc gtc ggc ctt gcc       296
Glu Ser Leu Leu Ile Leu Glu Tyr Leu Asp Asp Ala Val Gly Leu Ala
            75                  80                  85 ggc aac ggc aag ccc atc ctc ccc gca gac ccc tac agc cgc gcc gtc       344
Gly Asn Gly Lys Pro Ile Leu Pro Ala Asp Pro Tyr Ser Arg Ala Val
        90                  95                 100 gct cgc ttc tgg gcc gcc tat gtg aac gac aag ctg ttc cct tcg tgc       392
Ala Arg Phe Trp Ala Ala Tyr Val Asn Asp Lys Leu Phe Pro Ser Cys
    105                 110                 115 acc ggg atc ctc aag act acg aag cag gag gag aga gcc ggt aag atg       440
Thr Gly Ile Leu Lys Thr Thr Lys Gln Glu Glu Arg Ala Gly Lys Met
120                 125                 130 gag gag acc ctg tcc ggg ctc aga cac tta gaa gct gtc atg gcg gag       488
Glu Glu Thr Leu Ser Gly Leu Arg His Leu Glu Ala Val Met Ala Glu
135                 140                 145                 150 tgc tcc gaa ggg gag gcg gag gcg ccg ttc ttc ggt ggt gac gcc atc       536
Cys Ser Glu Gly Glu Ala Glu Ala Pro Phe Phe Gly Gly Asp Ala Ile
                155                 160                 165 ggg ttc ctc gac atc gcg ctc ggg tgc tat ctt ccc tgg ttt gag gca       584
Gly Phe Leu Asp Ile Ala Leu Gly Cys Tyr Leu Pro Trp Phe Glu Ala
            170                 175                 180 gca ggc cgc ctg gcc ggg ttg ggg ccg atc atc gac ccg gcg agg acg       632
Ala Gly Arg Leu Ala Gly Leu Gly Pro Ile Ile Asp Pro Ala Arg Thr
        185                 190                 195 ccg aaa cta gct gcg tgg gcg gag cgg ttc agc gtc gcc gag ccg atc       680
Pro Lys Leu Ala Ala Trp Ala Glu Arg Phe Ser Val Ala Glu Pro Ile
    200                 205                 210 aag gcg ctg ctg cct ggg gtc gac aag ctg gag gag tac atc act acg       728
Lys Ala Leu Leu Pro Gly Val Asp Lys Leu Glu Glu Tyr Ile Thr Thr
215                 220                 225                 230 gcg ctt tat cca aag tgg aac atc gcg gtc acc ggc aac taattaaaga        777
Ala Leu Tyr Pro Lys Trp Asn Ile Ala Val Thr Gly Asn
                235                 240 tcttgtcgtt ccactatggc aaaagaaata aaaaagggcg tcgttcgata accggcggag    837
gatctctgcc ttgtgagtag ctgttttcac gtcaagagtt gaactgttac tactaagtcg    897
ggtttctttt tgcgagggtt agtgggtcgt ggtcatgaat aatgcacagg cgtgcactct    957
cttcgatctg agttgtgata tgttgtttcg tgaataaatt gaagcgtcgt cgatcttgca   1017
tctaaaaaaa aaaaaaaaaa aaaaaa                                        1043
```

<210> SEQ ID NO 18

```
<211> LENGTH: 243
<212> TYPE: PRT
<213> ORGANISM: Triticum aestivum L.

<400> SEQUENCE: 18

Met Ala Gly Gly Glu Glu Leu Lys Leu Leu Gly Trp Trp Ala Pro Gly
 1               5                  10                  15

Val Ser Pro Tyr Val Leu Arg Ala Gln Met Ala Leu Ala Val Lys Gly
            20                  25                  30

Leu Ser Tyr Asp Tyr Leu Pro Glu Asp Arg Trp Ser Thr Ser Asp Leu
        35                  40                  45

Leu Ile Ala Ser Asn Pro Val Tyr Lys Lys Val Pro Val Leu Ile His
    50                  55                  60

Asn Gly Arg Pro Val Cys Glu Ser Leu Leu Ile Leu Glu Tyr Leu Asp
65                  70                  75                  80

Asp Ala Val Gly Leu Ala Gly Asn Gly Lys Pro Ile Leu Pro Ala Asp
                85                  90                  95

Pro Tyr Ser Arg Ala Val Ala Arg Phe Trp Ala Ala Tyr Val Asn Asp
            100                 105                 110

Lys Leu Phe Pro Ser Cys Thr Gly Ile Leu Lys Thr Thr Lys Gln Glu
        115                 120                 125

Glu Arg Ala Gly Lys Met Glu Glu Thr Leu Ser Gly Leu Arg His Leu
    130                 135                 140

Glu Ala Val Met Ala Glu Cys Ser Glu Gly Glu Ala Glu Ala Pro Phe
145                 150                 155                 160

Phe Gly Gly Asp Ala Ile Gly Phe Leu Asp Ile Ala Leu Gly Cys Tyr
                165                 170                 175

Leu Pro Trp Phe Glu Ala Ala Gly Arg Leu Ala Gly Leu Gly Pro Ile
            180                 185                 190

Ile Asp Pro Ala Arg Thr Pro Lys Leu Ala Ala Trp Ala Glu Arg Phe
        195                 200                 205

Ser Val Ala Glu Pro Ile Lys Ala Leu Leu Pro Gly Val Asp Lys Leu
    210                 215                 220

Glu Glu Tyr Ile Thr Thr Ala Leu Tyr Pro Lys Trp Asn Ile Ala Val
225                 230                 235                 240

Thr Gly Asn

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide primer to introduce NdeI site
      into translation start site of ICJ

<400> SEQUENCE: 19
aggtagttac atatggccgg agga                                            24
```

ISOLATED NUCLEIC ACIDS ENCODING A WHEAT GLUTATHIONE TRANSFERASE, PLANTS TRANSFORMED THEREWITH AND METHODS OF USE THEREOF

CROSS REFERENCE TO RELATED APPLICATIONS

This application is the U.S. National Stage of International Patent Application Ser. No. PCT/GB98/02802, Sep. 16, 1998, published in English as WO99/14337 on Mar. 25, 1999, which claims priority to Great Britain Patent Appl. Ser. No. 9719727.1, filed Sep. 16, 1997, the contents of which are incorporated herein in their entireties.

FIELD OF THE INVENTION

This invention relates to glutathione transferase (GST) subunits, to nucleic acid sequences encoding glutathione transferase subunits, and to uses of these glutathione transferases and coding sequences, especially in the field of plant biotechnology.

BACKGROUND OF THE INVENTION

Glutathione transferases (GSTs, EC. 2.5.1.18), also referred to as glutathione S-transferases, are multifunctional enzymes capable of catalysing the conjugation of electrophilic substrates with the tripeptide glutathione (GSH, gamma-glutamylcysteinylglycine). The electrophilic substrate may be of natural or synthetic origin, examples including endogenous stress-metabolites, drugs, pesticides and pollutants. Conjugation with GSH renders the compounds non-toxic and suitable for export from the cytosol and further metabolism. In addition to their activities in GSH conjugation, GSTs may have additional activities as glutathione peroxidases, catalysing the reduction of organic hydroperoxides to the corresponding alcohol according to the reaction:

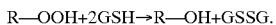

R—OOH+2GSH→R—OH+GSSG.

All known active GSTs are composed of two polypeptide subunits, with each subunit possessing a binding site for GSH and the electrophilic co-substrate. The two subunits may either be identical, giving rise to a homodimer, or dissimilar giving rise to heterodimers. GSTs may therefore be defined according to their source, or class, and their component subunits according to the nomenclature SpGST x-y, where Sp=source or class of GST; x and y describe the subunit types.

Each discrete subunit is encoded by a distinct gene, with many eukaryotes containing GST multigene families encoding multiple isoenzymes.

The plant in which GSTs have been characterised in the greatest detail is maize (*Zea mays* L.). The major maize GSTs are composed of three discrete subunits, termed I, II and III. These subunits associate together to form three isoenzymes containing the *Zea mays* GST I subunit, namely ZmGSTI-I, ZmGSTI-II and ZmGSTI-III as well as the homodimers ZmGSTII-II and ZmGSTIII-III. The nucieotide sequences of ZmGSTI, ZmGSTII and ZmGSTIII have been determined. In view of their relatedness in sequence, these maize GSTs have collectively been termed type I plant GSTs. Additional maize GSTs with activities toward herbicides have been described as ZmGSTV-V and ZmGSTV-VI. The sequence of ZmGSTV differs markedly from the other maize GSTs described to date, resembling the auxin-inducible GSTs from dicotyledenous plants which have been termed the type III GSTs.

The maize GST subunit types are associated with differing substrate specificities. The ZmGSTI subunit has broad-ranging, but low, activities toward chloro-s-triazine, chloroacetanilide and diphenyl ether herbicides. The ZmGSTII and ZmGSTIII subunits show greater specificity toward chloroacetanilides, while ZmGSTV and ZmGSTVI are highly active toward diphenyl ethers. The GST isoenzymes differ in their patterns of expression in the organs of maize. Thus, ZmGSTI-I and ZmGSTV-V are expressed in all plant parts, while ZmGSTI-II is root specific. The expression of the GST subunits is also differentially affected by herbicide safeners. These are compounds which enhance the tolerance of cereal crops to herbicides, in part, by increasing the expression of detoxifying enzymes such as GSTs. Thus, the ZmGSTII and ZmGSTV subunits accumulate in maize seedlings following treatment with the safeners dichlormid or benoxacor while the ZmGSTI and ZmGSTIII subunits are only modestly enhanced by safeners.

Far less is known regarding GSTs in plant species other than maize. GSTs with activities toward non-herbicide substrates have been identified in some plants, and mRNAs apparently encoding GSTs have been shown to be expressed in plants including carnation, tobacco and thale cress (*Arabidopsis thaliana*). However, isoenzymes with activities toward herbicides have only been definitively identified in soybean, pea and pine trees. Of these, only in soybean has the nucleotide coding sequences of the herbicide-detoxifying GST been reported.

GSTs in plants have also been shown to have secondary activities as glutathione peroxidases, able to reduce organic hydroperoxides, such as fatty acid hydroperoxides to the corresponding monohydroxy alcohols. GSTs with glutathione peroxidase activity have been isolated from peas, soybean, *A. thaliana* and wheat flour. Since fatty acid hydroperoxides are a cornmon result of membrane peroxidation imposed during oxidative stress, glutathione peroxidases provide an important cytoprotective function in preventing the accumulation of fatty acid hydroperoxides and their subsequent degradation to toxic aldehydes. Glutathione peroxidases may therefore have a vital function in protecting plant cells from oxidative stress. The intervention of glutathione peroxidases in lipid peroxidation has also been cited as a determinant of flour quality in wheat.

Of particular relevance to this invention is the lack of knowledge concerning the GSTs of wheat (*Triticum aestivum* L.).

Some information is available from experiments on whole plants and plant extracts. Several herbicides including examples of the chloroacetanilides, as well as dimethenamid and fenoxaprop-ethyl undergo GSH conjugation in the course of their detoxification in wheat. Also, in crude plant extracts OST activities toward chloroacetanilide herbicides, dimethenamid and fenoxaprop-ethyl have been demonstrated.

There have been very few reports of the purification of GSTs from wheat. A GST was purified from wheat flour, and described as a homodimer of 27.5 kDa polypeptides with activity toward the non-herbicide substrate 1-chloro-2,4-dinitrobenzene (CDNB) and glutathione peroxidase activity toward fatty acid hydroperoxides. A safener-induced GST with activity toward CDNB and dimethenamid, termed GSTTaI-I, has been purified and partially sequenced from the wheat progenitor species *Triticum tauschii*, (Reichers et al, (1997), Plant Physiology, 114, pages 1461 to 1470).

Moreover, very little is known regarding GST genes in wheat. An mRNA originally described as wir5, which showed sequence similarity to the type 1 maize GSTs, was identified as accumulating in wheat leaves during the onset of acquired resistance to powdery mildew (*Erysiphe graminis*). The gene was termed gstA1 and shown to be similar in genomic organisation to maize ZmGST1. The gstA1 polypeptide was expressed in recombinant bacteria and shown to have an apparent molecular mass of 29 kDa. The respective enzyme showed GST activity towards the non-herbicide CDNB, though the activity toward other substrates and activity as a glutathione peroxidase was not reported. An antibody was raised to the recombinant GstA1 and used in Western blotting experiments to show that this GST was specifically induced in wheat leaves by pathogen attack. In contrast, a distinct class of GSTs composed of 25 kDa and 26 kDa subunits, which were recognised by an antiserum raised to undefined GSTs in maize, accumulated following exposure to cadmium and the herbicides atrazine, alachlor and paraquat. The activities of these xenobiotic-inducible GSTs in wheat and the corresponding nucleotide sequences were not reported. A cDNA correponding to am mRNA encoding a safener-inducible type III GST has been isolated from *Triticum tauschii* and had the same amino acid sequence as GSTTaI-I, (Reicher et al, (1997), Plant Physiology, 1141, page 1568).

Thus, although wheat is an important crop plant, there has been little molecular characterisation of wheat GSTs or their genes and, to date, only two purified GSTs and two GST gene sequences, gstA1 and GSTTa1 available.

Significantly, neither purified recombinant GST proteins expressed from gene gstA1 or GSTTa1 were reported to exhibit activity towards herbicides. Hence, none of the previous work on wheat GSTs actually provides any means of achieving herbicide resistance based on the function of wheat GSTs.

SUMMARY OF THE INVENTION

We have purified four GST isoenzymes with activity toward herbicides from wheat shoots treated with the herbicide safener fenchlorazole-ethyl and have identified four distinct subunits. In safener-treated shoots, we have found that the predominant GST subunit is a 25 kDa polypeptide, which has been termed *Triticum aestivum* GST 1 (TaGST1). Additionally, two distinct 26 kDa subunits have been identified and termed TaGST2 and TaGST3 and a 24 kDa subunit, termed TaGST4. These subunits associate together to form the active dimeric isoenzymes TaGST1-1, TaGST1-2, TaGST1-3 and TaGST1-4.

In our experiments, the expression of all four isoenzymes was affected by the herbicide safener fenchlorazole-ethyl, although each one responds in a somewhat different way. The TaGST1-1 isoenzyme is the major GST present in the leaves of untreated wheat seedlings, and its expression is increased by approximately 50% following exposure to fenchlorazole-ethyl. TaGST1-4 is expressed at low levels in untreated shoots and its expression is greatly increased by safener application, while TaGST1-2 and TaGST1-3 are only observed following treatment with the safener. All four of these GST isoenzymes have broad-ranging activities toward xenobiotic substrates and all four demonstrate activity towards herbicides and additional activities as glutathione peroxidases able to reduce organic hydroperoxides, with TaGST1-4 being the most active in this respect. Each isoenzyme also has specific properties. Thus, for example, detoxification of one particular herbicide, fenoxaprop-ethyl, is associated with the more strongly safener-inducible TaGST1-2, TaGST1-3 and TaGST1-4 heterodimers, rather than with the TaGST1-1 homodimer.

Furthermore, we have identified, cloned and sequenced cDNAs for the major type III GSTs in wheat, together with cDNAs encoding a range of type I GSTs, all active in herbicide metabolism. This is fundamental to understanding the GST detoxification system in wheat and to exploiting it to generate transgenic herbicide-resistant plants expressing wheat GSTs. In many previous studies, GST activity could not be linked to specific genes, precluding this approach.

From the sequences of the cDNAs the amino acid sequences of the GST subunits themselves has been deduced.

Accordingly, the invention provides:

a polynucleotide encoding a glutathione transferase (GST) subunit, which polynucleotide comprises a coding sequence capable of hybridising selectively to the coding sequence of SEQ ID No. 1, 3, 5, 7, 9, 11, 13, 15 or 17 to the complement of one of those sequences.

The invention also provides:

a polypeptide which is a GST subunit and comprises the amino acid sequence of SEQ ID No. 2, 4, 6, 8, 10, 12, 14, 16 or 18 or a sequence substantially homologous thereto, or a fragment of either said sequence.

The invention also provides:

a dimeric protein comprising two GST subunits, wherein at least one subunit is a polypeptide of the invention.

The invention also provides:

a chimeric gene comprising a polynucleotide of the invention operably linked to regulatory sequences that allow expression of the coding sequence in a host cell.

The invention also provides:

a vector comprising a polynucleotide of the invention or a chimeric gene of the invention.

The invention also provides:

a cell transformed or transfected with a vector of the invention.

The invention also provides:

a cell having, integrated into its genome, a chimeric gene of the invention.

The invention also provides:

a process for the production of a polypeptide of the invention, which process comprises:

(a) cultivating a cell of the invention under conditions that allow the expression of the polypeptide; and (b) recovering the expressed polypeptide.

The invention also provides:

a process for the production of a dimeric protein of the invention, which process comprises:

(a) cultivating a cell of the invention under conditions that allow:

(i) the expression of the polypeptide of the invention and, if a further polynucleotide sequence as defined herein is present, optionally the expression of a further GST subunit encoded by a further polynucleotide, and (ii) the association of the GST subunit polypeptide of the invention with another GST subunit polypeptide to form a dimeric protein of the invention; and (b) recovering the dimeric protein so formed.

The invention also provides:

a method of obtaining a transgenic plant cell comprising:

(a) transforming a plant cell with an expression vector of the invention to give a transgenic plant cell, and optionally, (a') transforming the cell with one or more further polynucleotide sequences coding for a GST subunit, operably linked to regulatory elements that allow expression of the subunit in the cell.

The invention also provides:

a method of obtaining a first-generation transgenic plant comprising:
- (b) regenerating a transgenic plant cell transformed with a vector of the invention to give a transgenic plant.

The invention also provides:

a method of obtaining a transgenic plant seed comprising:
- (c) obtaining a transgenic seed from a transgenic plant obtainable by regenerating a transgenic plant cell transformed with a vector of the invention.

The invention also provides:

a method of obtaining a transgenic progeny plant comprising obtaining a second-generation transgenic progeny plant from a first-generation transgenic plant obtainable by regenerating a transgenic plant cell transformed with a vector of the invention, and optionally obtaining transgenic plants of one or more further generations from the second-generation progeny plant thus obtained.

The invention also provides:

a method of obtaining a transgenic progeny plant comprising obtaining a second-generation transgenic progeny plant from a first-generation transgenic plant obtainable by regenerating a transgenic plant cell transformed with a vector of the invention comprising:
- (c) obtaining a transgenic seed from a first-generation transgenic plant obtainable by regenerating a transgenic plant cell transformed with a vector of the invention, then obtaining a second-generation transgenic progeny plant from the transgenic seed;

and/or
- (d) propagating clonally a first-generation transgenic plant obtainable by regenerating a transgenic plant cell transformed with a vector of the invention to give a second-generation progeny plant;

and/or
- (e) crossing a first-generation transgenic plant obtainable by regenerating a transgenic plant cell transformed with a vector of the invention with another plant to give a second-generation progeny plant;

and optionally;
- (f) obtaining transgenic progeny plants of one or more further generations from the second-generation progeny plant thus obtained.

The invention also provides:

a transgenic plant cell, first-generation plant, plant seed or progeny plant obtainable by a method of the invention.

The invention also provides:

a transgenic plant or plant seed comprising plant cells of the invention.

The invention also provides:

a transgenic plant cell callus comprising plant cells of the invention, or obtainable from a transgenic plant cell, first-generation plant, plant seed or progeny plant of the invention.

The invention also provides:

use of a polynucleotide of the invention as a selectable marker for detecting transformation of a plant cell.

The invention also provides:

a nucleic acid construct comprising:
- (a) a polynucleotide of the invention operably linked to regulatory elements that allow expression of the coding sequence in a plant cell; and
- (b) a site into which a further polynucleotide comprising a coding sequence can be inserted.

The invention also provides:

a vector comprising such a construct.

The invention also provides:

a method of transforming a plant cell or of obtaining a plant cell culture or transgenic plant comprising:
- (a) providing an untransformed plant cell which is susceptible to a herbicide whose herbicidal activity is reduced by a dimeric protein of the invention;
- (b) transforming the plant cell with a vector comprising:
  - (i) a polynucleotide of the invention operably linked to regulatory elements that allow expression of the coding sequence in a plant cell; and
  - (ii) a site into which a further polynucleotide comprising a coding sequence can be inserted;
- (c) cultivating the transformed cell under conditions that allow the expression of the polynucleotide (a) in the construct; and/or
- (c') regenerating the cell to give a cell culture or plant such that the polynucleotide (a) in the construct is expressed; and
- (d) contacting the cell, cell culture or plant with the herbicide whose herbicidal activity is reduced by the dimeric protein of the invention, and to which the untransformed plant cell was susceptible; and
- (e) selecting cells, cell cultures or plants that are less susceptible to the herbicide than are corresponding untransformed cells, cell cultures or plants.

The invention also provides:

use of a dimeric protein of the invention in a method of identifying compounds capable of metabolism by a GST.

The invention also provides:

a method of identifying compounds capable of being metabolised by a glutathione transferase comprising:
- (a) contacting a candidate compound suspected of being capable of being metabolised by glutathione transferase with glutathione (GSH) in the presence of a dimeric protein of the invention; and
- (b) determining whether or not metabolism of the candidate compound takes place.

The invention also provides:

compounds identified by such methods.

The invention also provides:

a kit for detecting compounds capable of being metabolised by a GST comprising:
- (a) reduced glutathione, hydroxymethylglutathione or homoglutathione;

and
- (b) a dimeric protein of the invention.

The invention also provides:

an antibody which specifically recognises a polypeptide or dimeric protein of the invention.

The invention also provides:

a nucleic acid probe which selectively hybridises to the sequence of SEQ ID No. 1, 3, 5, 7, 9, 11, 13, 15 or 17.

The invention also provides:

a method of identifying compounds that induce GST expression in graminaceous plants comprising:
- (a) contacting a graminaceous plant, or a cell or cell culture thereof, with a candidate compound suspected of being capable of inducing GST expression; and
- (b) determining the level of GST expression in the plant, cell or cell culture.

The invention also provides:

compounds identified by such methods.

The invention also provides:

a kit for identifying compounds that induce GST expression in plants by such a method, which kit comprises an antibody of the invention.

The invention also provides:

a method of determining the GST level in a sample of seed or flour comprising:
  (i) determining the level of GST protein present by using an antibody of the invention; or
  (ii) determining the level of GST mRNA present using a probe of the invention.

The invention also provides:

a method of controlling the growth of weeds at a locus where a transgenic plant of the invention is being cultivated, which method comprises applying to the locus a herbicide whose herbicidal properties are reduced by a dimeric protein of the invention.

Figure 1A:
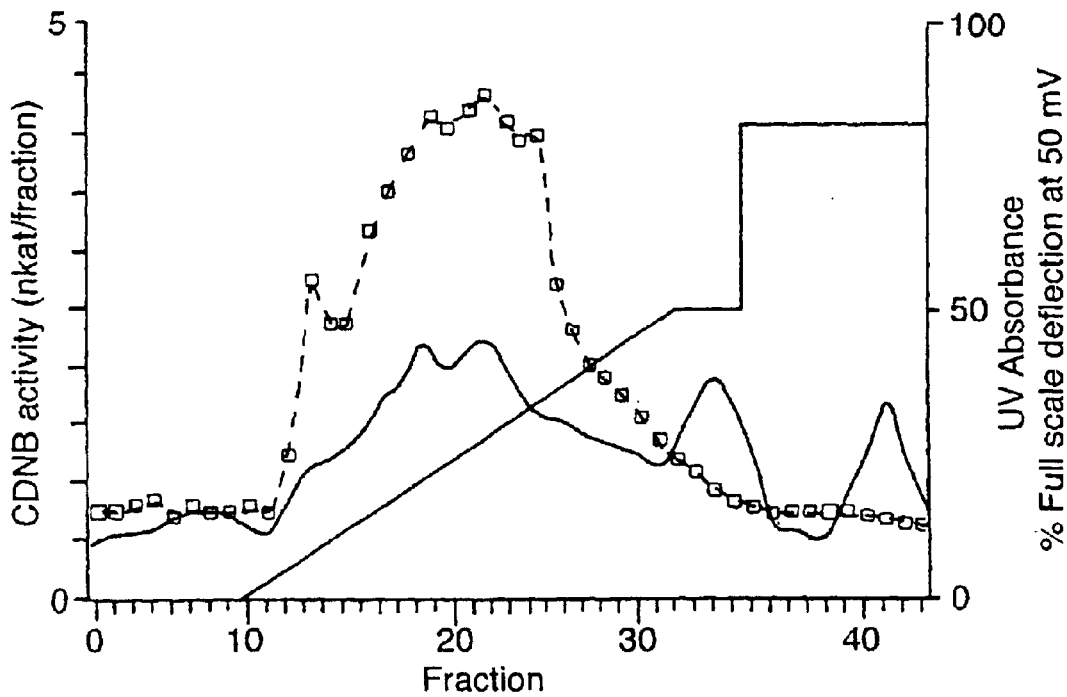
FIG. 1. Anion-exchange chromatography of affinity-purified wheat GSTs.

Chromatography of A: affinity-purified polar GSTs; and B: affinity-purified hydrophobic GSTs on Hi-Trap Q-Sepharose columns eluted with the increasing NaCl gradient shown. The eluent was monitored for $A_{280}$ as shown with the unbroken line and individual fractions assayed for GST activity.

FIG. 2. HPLC analysis of wheat GST subunits.

Reversed-phase HPLC analysis of polypeptide subunits present in A, affinity-purified polar GSTs; B, affinity-purified hydrophobic GSTs; C, the isoenzyme TaGST1-1, resolved by anion-exchange chromatography of the affinity-purified polar GSTs.

DETAILED DESCRIPTION OF THE INVENTION

Polynucleotides

The invention provides polynucleotides comprising sequences encoding novel GST subunits, SEQ ID Nos 1, 3, 5, 7, 9, 11, 13, 15 and 17 and sequences that hybridise selectively to these coding sequences thereof or their complementary sequences. It also provides polynucleotide fragments of these sequences that encode polypeptides having GST activity, as defined herein.

A polynucleotide of the invention is capable of hybridising selectively with the coding sequence of SEQ ID No. 1, 3, 5, 7, 9, 11, 13, 15 or 17 or to the sequence complementary to one of those coding sequences. Polynucleotides of the invention include variants of the coding sequence of SEQ ID No. 1, 3, 5, 7, 9, 11, 13, 15 or 17 which can function as GSTs, when dimerised with another GST subunit. Typically, a polynucleotide of the invention is a contiguous sequence of nucleotides which is capable of selectively hybridising to the coding sequence of SEQ ID. No. 1, 3, 5, 7, 9, 11, 13, 15 or 17 or to the complement of that coding sequence.

A polynucleotide of the invention can hybridise to coding sequence of SEQ ID No. 1, 3, 5, 7, 9, 11, 13, 15 or 17 at a level significantly above background. Background bybridisation may occur, for example, because of other cDNAs present in a cDNA library. The signal level generated by the interaction between a polynucleotide of the invention and the coding sequence of SEQ ID No. 1, 3, 5, 7, 9, 11, 13, 15 or 17 is typically at least 10 fold, preferably at least 100 fold, as intense as interactions between other polynucleotides and the coding sequence of SEQ ID No. 1, 3, 5. 7, 9, 11, 13, 15 or 17. The intensity of interaction may be measured, for example, by radiolabelling the probe, e.g. with $^{32}P$ Selective hybridisation is typically achieved using conditions of medium to high stringency (for example 0.03M sodium chloride and 0.03M sodium citrate at from about 50° C. to about 60° C.).

A nucleotide sequence capable of selectively hybridising to the DNA coding sequence of SEQ ID No. 1, 3, 5, 7, 9, 11, 13, 15 or 17 or to the sequence complementary to one of those coding sequences will be generally at least 70%, preferably at least 80 or 90% and more preferably at least 95%, 98% or 99%, homologous to the coding sequence of SEQ ID No. 1, 3, 5, 7, 9, 11, 13, 15 or 17 or the complement of one of those sequences over a region of at least 20, preferably at least 30, for instance at least 40, 60 or 100 or more contiguous nucleotides.

Any combination of the above mentioned degrees of homology and minimum sizes may be used to define polynucleotides of the invention, with the more stringent combinations (i.e. higher homology over longer lengths) being preferred. Thus for example a polynucleotide which is at least 90% homologous over 25, preferably over 30 nucleotides forms one aspect of the invention, as does a polynucleotide which is at least 95% homologous over 40 nucleotides.

Polynucleotides of the invention may comprise DNA or RNA. They may also be polynucleotides which include within them synthetic or modified nucleotides. A number of different types of modification to polynucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or lifespan of polynucleotides of the invention.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will preferably be at least 10, preferably at least 15 or 20, for example at least 25, 30 or 40 nucleotides in length.

Polynucleotides such as a DNA polynucleotide and primers according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a stepwise manufacture of the desired nucleic acid sequence one nucleotide at a time. Techniques for accomplishing this using automated techniques are readily available in the art.

Genomic clones corresponding to the cDNAs of SEQ ID No. 1, 3, 5, 7, 9, 11, 13, 15 and 17 containing, for example introns and promoter regions are also aspects of the invention and may also be produced using recombinant means, for example using PCR (polymerase chain reaction) cloning techniques, starting with genomic DNA from a wheat (*Triticum aestivum L.*), cell, e.g. a wheat shoot cell or a cell of a plant of a related Triticum species, for example as described by Feldman et al., (Scientific American, (1981), vol. 244(1) pages 98 to 109).

Although in general the techniques mentioned herein are well known in the art, reference may be made in particular to Sambrook et al, 1989, Molecular Cloning: a laboratory manual.

Polynucleotides which are not 100% homologous to the sequences of the present invention but fall within the scope of the invention can be obtained in a number of ways.

Other allelic variants of the wheat sequences of SEQ ID Nos. 1,3, 5, 7, 9, 11, 13, 15 and 17 including those from *Triticum aestivum L.* species itself related to *Triticum aestivum L.* (cf Feldman et al, supra) may be obtained for example by probing genomic DNA libraries made from a range of wheat cells, using probes as described above.

In addition, other plant homologues of SEQ ID Nos. 1, 3, 5, 7, 9, 11, 13, 15 and 17 may be obtained and such homologues and fragments thereof in general will be capable of selectively hybridising to the coding sequence of SEQ ID No. 1, 3, 5, 7, 9, 11, 13, 15 or 17 or its complement. Such sequences may be obtained by probing cDNA or genomic libraries from other plant species with probes as described above. Degenerate probes can be prepared by means known in the art to take into account the possibility of degenerate variation between the DNA sequences of SEQ ID Nos. 1, 3, 5, 7, 9, 11, 13, 15 and 17 and the sequences being probed for under conditions of medium to high stringency (for example 0.03M sodium chloride and 0.03M sodium citrate at from about 50° C. to about 60° C.).

Allelic variants and species homologues may also be obtained using degenerate PCR which will use primers designed to target sequences within the variants and homologues encoding likely conserved amino acid sequences. Likely conserved sequences can be predicted from aligning the amino acid sequences of the invention (SEQ ID No. 2, 4, 6, 8, 10, 12, 14, 16 and 18) with that of other similar GST subunit sequences. The primers will contain one or more degenerate positions and will be used at stringency conditions lower than those used for cloning sequences with single sequence primers against known sequences.

Alternatively, such polynucleotides may be obtained by site directed mutagenesis of SEQ ID Nos. 1, 3, 5, 7, 9, 11, 13, 15 or 17 sequences or allelic variants thereof. This may be useful where, for example, silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The invention further provides double stranded polynucleotides comprising a polynucleotide of the invention and its complement.

Polynucleotides, probes or primers of the invention may carry a revealing label. Suitable labels include radioisotopes such as $^{32}P$ or $^{35}S$, enzyme labels, or other protein labels such as biotin. Such labels may be added to polynucleotides, probes or primers of the invention and may be detected using techniques known per se.

The present invention also provides polynucleotides encoding the polypeptides of the invention described below. Because such polynucleotides will be useful as sequences for recombinant production of polypeptides of the invention, it is not necessary for them to be selectively hybridisable to the coding sequence of sequence SEQ ID Nos. 1, 3, 5, 7, 9, 11, 13, 15 or 17 although this will generally be desirable. Otherwise, such polynucleotides may be labelled, used, and made as described above if desired. Polypeptides of the invention are described below.

Particularly preferred polynucleotides of the invention are those of SEQ ID No. 1, 3, 5, 7, 9, 11, 13, 15 or 17 and the polynucleotides that are the coding regions within those sequences i.e. the regions which encode the polypeptides of SEQ ID No. 2, 4, 6, 8, 10, 25 12, 14, 16 or 18.

Polypeptides

A polypeptide of the invention consists essentially of the amino acid sequence set out in SEQ ID No. 2, 4, 6, 8, 10, 12, 14, 16 or 18 or a substantially homologous sequence, or of a fragment of either of these sequences. In general, the naturally occurring amino acid sequences shown in SEQ ID Nos. 2, 4, 6, 8, 10, 12, 14, 16 or 18 are preferred. However, the polypeptides of the invention include homologues of the natural sequences, and fragments of the natural sequences and of their homologues, which have GST activity.

The polypeptides of the invention are glutathione transferase (GST) subunits. The invention also provides dimeric proteins comprising two GST subunits wherein at least one subunit is a polypeptide of the invention.

Thus, the polypeptides of the invention are normally functionally active as GSTs when dimerised with another GST subunit. Thus, dimeric proteins of the invention are capable of catalysing the conjugation of the tripeptide glutathione (GSH, gamma-glutamylcysteinyl glycine) and/or related derivatives to an electrophilic substrate of natural or synthetic origin. Related derivatives include homoglutathione (gamma-glutamylcysteinyl alanine) and hydroxymethylglutathione (gamma-glutamylcysteinyl serine).

Optionally, they may also have one or more of the other properties of naturally occurring GSTs including glutathione peroxidase activity as defined above.

Preferably, they have GST activity towards one or more herbicide substrates. For example, they may have activity towards one or more of the following herbicides: Fluorodifen, Fenoxaprop-ethyl, Metolachlor, Alpha-Metolachlor, Acetochlor, Alachlor, Pretilachlor, Fluthiamid, Dimethenamid, S-Dimethenamid, Flupyrsulfuron-methyl, Triflusulfuron-methyl, Acifluorfen, Chlorimuron-ethyl, Fomesafen, Atrazine, Simazine, Cyanazine and the sulphatide metabolite of Metribuzin. Particularly preferred herbicides include Fenoxaprop-ethyl, Flupyrsulfuron-methyl, Fluthiamid, Acetochlor, Metolachlor and Alpha-Metolachlor.

Most preferably, a dimeric protein of the invention is able to catalyse the conjugation of GSH to one or more of the following herbicide substrates: Fenoxaprop-ethyl, Flupyrsulfuron-methyl, fluthiamid. Acetochlor, Metolachlor and Alpha-Metolachlor.

Optionally, a dimeric protein of the invention may be able to catalyse the conjugation of GSH to one or more non-herbicide substrates, for example CDNB. They may also have activity towards phytotoxic non-herbicide substrates.

Optionally, monomeric polypeptides of the invention may have GST activity as defined above, even when not dimerised.

In particular, a polypeptide of the invention may comprise:

(a) the polypeptide sequence of SEQ ID No. 2, 4, 6, 8, 10, 12, 14, 16 or 18;

(b) an allelic variant or species homologue thereof; or (c) a protein at least 70 80, 90, 95, 98 or 99% homologous to (a) or (b).

An allelic variant will be a variant which will occur naturally in a plant and which will function in a substantially similar manner to the protein of SEQ ID No. 2, 4, 6, 8, 10, 12, 14, 16 or 18, as defined above. Similarly, a species homologue of the protein will be the equivalent protein which occurs naturally in another plant species which can function as GST. Such a homologue may occur in plants other than wheat, particularly monocotyledonous plants such as related Triticum species, rice, maize, oats, rye, barley, triticale or sorghum. Within any one species, a homologue may exist as several allelic variants, and these will all be considered homologues of the protein of SEQ ID No. 2, 4, 6, 8, 10, 12, 14, 16 or 18.

Allelic variants and species homologues can be obtained by following the procedures described herein for the production of the polypeptides of SEQ ID No. 2, 4, 6, 8, 10, 12, 14, 16 and 18 and performing such procedures on a suitable cell source e.g. a cell of a wheat genotype carrying an allelic variant, or a cell of a plant of a different another species. It will also be possible to use a probe as defined above nucleotide sequence to probe libraries made from plant cells in order to obtain clones encoding the alleic or species variants. The clones can be manipulated by conventional techniques to generate a polypeptide of the invention which can then be produced by recombinant or synthetic techniques known per se.

A polypeptide of the invention is preferably at least 70% homologous to the protein of SEQ ID No. 2, 4, 6, 8, 10, 12, 14, 16 or 18, more preferably at least 80 or 90% and more preferably still at least 95%, 97% or 99% homologous thereto over a region of at least 20, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology").

The sequence of the polypeptides of SEQ ID Nos 2, 4, 6, 8, 10, 12, 14, 16 and 18 and of allelic variants and species homologues can thus be modified to provide polypeptides of the invention.

Amino acid substitutions may be made, for example from 1, 2 or 3 to 10, 20 or 30 substitutions. The modified polypeptide generally retains activity as a GST, as defined herein. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Polypeptides of the invention also include fragments of the above-mentioned full length polypeptides and variants thereof, including fragments of the sequence set out in SEQ ID No. 2, 4, 6, 8, 10, 12, 14, 16 and 18. Such fragments typically retain activity as a GST.

Other preferred fragments include those which include an epitope. Suitable fragments will be at least about 5, e.g. 10, 12, 15 or 20 amino acids in size. Polypeptide fragments of the polypeptides of SEQ ID Nos. 2, 4, 6, 8, 10, 12, 14, 16 and 18, and allelic and species variants thereof may contain one or more (e.g. 2, 3, 5, or 10) substitutions, deletions or insertions, including conserved substitutions. Epitopes may be determined either by techniques such as peptide scanning techniques already known in the art. These fragments will be useful for obtaining antibodies to polypeptides and dimeric proteins of the invention.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

Polypeptides of the invention may be modified for example by the addition of Histidine residues or a T7 tag to assist their identification or purification or by the addition of a signal sequence to promote their secretion from a cell.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

Polypeptides and dimeric proteins of the invention may be chemically modified, e.g. post-translationally modified. For example, they may be glycosylated or comprise modified amino acid residues. Such modified polypeptides and proteins fall within the scope of the terms "polypeptide" and "dimeric protein" of the invention.

Dimeric Proteins

The invention also provides dimeric proteins having two GST subunits wherein at least one of the two subunits is a polypeptide of the invention. These dimeric proteins may have two identical subunits of the invention, i.e. they may be homodimeric. Alternatively, they may have two dissimilar subunits; i.e. they may be heterodimeric.

In heterodimers, the two subunits may both be polypeptides of the invention. Alternatively, one subunit may be a polypeptide of the invention, whilst the other is a different GST subunit.

Thus, for example, heterodimeric proteins of the invention may have one subunit which is a polypeptide of the invention, and one which is a known GST subunit from maize (e.g. ZmGSTI, ZmGSTII, ZmGSTIII, ZmGSTIV, ZmGSTV or ZmGSTVI: see above), or another species.

Preferably, the dimeric proteins have two subunits that are polypeptides of the invention. Various combinations of polypeptides of the invention are possible. Preferred combinations include:

TaGST1-1 (SEQ ID No. 2/SEQ ID No. 2);
TaGST1-2 (SEQ ID No. 2/SEQ ID No. 16);
TaGST1-3 (SEQ ID No. 2/SEQ ID No. 18);

being representative of the major combinations found in GSTs in safener-treated wheat.

The invention also provides dimeric proteins having two subunits as described above which are fusion proteins. In these fusion proteins, the two subunits are joined by a linker polypeptide. Any linker may be used as long as it does not interfere significantly with the correct association of the two subunits or with the GST activity of the dimer. Such fusion proteins will typically be prepared by joining together the polynucleotides encoding the two monomers in the correct reading frame, then expressing the composite polynucleotide coding sequence under the control of regulatory sequences as defined herein. These composite polynucleotide coding sequences are a further aspect of the invention, as are chimeric genes and vectors comprising them, methods of producing them by recombinant means, and cells and plants comprising such vectors or chimeric genes. It will be understood that dimeric proteins of the invention may be such fusion proteins.

Vectors and Chimeric Genes

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and cultivating the host cell under conditions which bring about replication of the vector. The vector may be recovered from the host cell. Suitable host cells are described below in connection with expression vectors. Bacterial cells, especially E. Coli are preferred.

Expression Vectors

Preferably, a polynucleotide of the invention in a vector is operably linked to regulatory sequences capable of effecting the expression of the coding sequence by the host cell, i.e. the vector is an expression vector. Such expression vectors can be used to express the polypeptides of the invention.

The term "operably linked" refers to a juxtaposition wherein the components described are in a relationship permitting them to function in their intended manner. A regulatory sequence "operably linked" to a coding sequence is positioned in such a way that expression of the coding sequence is achieved under conditions compatible with the regulatory sequences.

Such vectors may be introduced into a suitable host cell to provide for expression of a polypeptide or polypeptide fragment of the invention, as described below.

The vectors may be for example, plasmid, virus or phage vectors provided with an origin of replication, preferably a promoter for the expression of the said polynucleotide and optionally an enhancer and/or a regulator of the promoter. For expression in plant cells, one preferred enhancer is the Tobacco etch virus (TEV) enhancer. A terminator sequence may also be present, as may a polyadenylation sequence. The vectors may contain one or more selectable marker genes, for example an ampicillin resistance gene in the case of a bacterial plasmid or a neomycin resistance gene (e.g. nptI or nptII) or methotrexate resistance gene for a plant vector. Vectors may be used in vitro, for example for the production of RNA or used to transfect or transform a host cell. The vector may also be adapted to be used in vivo, for example for generation of transgenic plants of the invention.

So far as plasmid vectors are concerned, plasmids derived from the Ti plasmid of Agrobacterium tumefaciens are especially preferred, as are plasmids derived from the Ri plasmid of Agrobacterium rhizogenes.

A further embodiment of the invention provides host cells transformed or transfected with the vectors for the replication and expression of polynucleotides of the invention. The cells will be chosen to be compatible with the said vector and may for example be prokaryotic (bacterial), plant, yeast, insect or mammalian cells, bacterial and plant cells being preferred.

Polynucleotides according to the invention may also be inserted into the vectors described above in an antisense orientation in order to provide for the production of antisense RNA. Antisense RNA or other antisense polynucleotides may also be produced by synthetic means. Such antisense polynucleotides may be used in a method of controlling the levels of GSTs having the sequence of SEQ ID No. 2, 4, 6, 8, 10, 12, 14, 16 or 18 or their variants or species homologues in planta.

Promoters and other regulatory elements may be selected to be compatible with the host cell for which the expression vector is designed.

Promoters suitable for use in plant cells may be derived, for example, from plants or from bacteria that associate with plants or from plant viruses. thus, promoters from Agrobacterium spp. including the nopaline synthase (nos), octopine synthase (ocs) and mannopine synthase (mas) promoters are preferred. Also preferred are plant promoters such as the ribulose bisphosphate small subunit promoter (rubisco ssu), and the phaseolin. promoter. Also preferred are plant viral promoters such as the cauliflower mosaic virus (CAMV) 35S and 19S promoters.

Depending on the pattern of expression desired, promoters may be constitutive or inducible. For example, strong constitutive expression in plants can be obtained with the CAMV 35S or rubisco ssu promoters. Also, tissue-specific or stage-specific promoters may be used to target expression of polypeptides of the invention to particular tissues in a transgenic plant or to particular stages in its development. Chemically inducible promoters such as those activated by herbicide safeners may also be used, for example the maize GST 27 promoter (WO97/11189), the maize In2-1 promoter (WO90/11361), the maize In2-2 promoter (De Veylder et al, (1997), Plant Cell Physiology, Vol.38, pages 568 to 577.

Especially where expression in plant cells is desired, other regulatory signals may also be incorporated in the vector, for example a terminator and/or polyadenylation site. One preferred terminator is the nos terminator although other terminators functional is the nos terminator in plant cells may also be used.

Additionally, sequences encoding secretory signals or transit peptides may be included. On expression, these elements direct secretion from the cell or target the polypeptide of the invention to a particular location within the cell. For example, sequences may be added to target the expressed polypeptide to the nucleus or plastids (e.g. chloroplasts) of a plant cell.

Chimeric Genes

The invention also provides chimeric genes suitable for securing the expression of polypeptides of the invention in a host cell, preferably a plant cell. These comprise a polynucleotide of the invention, operably linked to regulatory sequences that allow its expression in a host cell, preferably a plant cell.

Typically, therefore, a chimeric gene comprises the following elements in 5' to 3' orientation: a promoter functional in a host (preferably plant) cell, as defined above, a polynucleotide of the invention and a terminator functional in said cell, as defined above. Other elements, for example an enhancer, may also be present. These chimeric genes may be incorporated into vectors, as defined above.

Expression in Host Cells

Expression vectors of the invention may be introduced into host cells using conventional techniques including calcium phosphate precipitation, DEAE-dextran transfection, or electroporation. For plant cells, preferred transformation techniques include electroporation of plant protoplasts, transformation by Agrobacterium tumefaciens and particle bombardment. Particle bombardment is particularly preferred for transformation of monocot cells.

Expression in the host cell may be transient although, preferably, integration of the polynucleotide or chimeric gene of the invention into the cell's genome is achieved.

Suitable cells include cells in which the above-mentioned vectors may be expressed. These include microbial cells such as bacteria such as E. coli, plant cells, mammalian cells such as CHO cells, COS7 cells or Hela cells, insect cells or yeast such as Saccharomyces. Bacterial and plant cells are preferred.

Optionally, cells of the invention may comprise one or more further polynucleotide sequences encoding a GST subunit, operably linked to regulatory sequences, as defined above, that allow expression of the subunit in the cell. Such polynucleotide sequences may be further polynucleotides of the invention or they may encode other GST subunits as defined above with respect to dimeric proteins.

Such polynucleotides may be naturally present in the cell, e.g. if it is a plant cell or they may be introduced artificially, e.g. as defined above.

Such cells allow the production of heterodimeric proteins of the invention where the polynucleotides encode different GST subunits, or the production of monomeric polypeptides of the invention and/or homodimeric proteins of the invention in greater quantities. For example, they may allow the expression of active heterodimeric enzymes.

Cell culture will take place under standard conditions. Commercially available cultural media for cell culture are widely available and can be used in accordance with manufacturers' instructions.

Processes for Production of Polypeptides and Dimeric Proteins

The invention provides processes for the production of polypeptides and dimeric proteins of the invention by recombinant means.

Generally, monomeric GST subunits of the invention spontaneously dimerise to form homodimers and/or heterodimers of the invention. Thus, in general, expression of polypeptides of the invention gives rise to dimers in the first instance. These dimers may be the desired product; alternatively, it may be desirable to separate the monomers. For example, as described below, it may be desired to separate the monomeric subunits of a homodimer in order to combine them with different monomeric subunits, thereby yielding heterodimers.

Processes for the production of polypeptides of the invention may comprise:

(a) cultivating a transformed cell as defined above under conditions that allow the expression of the polypeptide; and preferably (b) recovering the expressed polypeptide.

For example, the expressed monomeric peptides may be recovered by denaturation of dimers formed by them, which separates the subunits. Then, the monomers can be recovered and renatured. Typically, they will then redimerise.

Processes for production of dimeric proteins of the invention may comprise:

(a) cultivating a transformed cell as defined above under conditions that allow (i) the expression of the polypeptide of the invention and, if a further GST subunit-encoding sequence as defined above is present, optionally the expression of a further GST subunit encoded by the further sequence and preferably (ii) the association of the GST subunit polypeptide of the invention with another identical GST subunit polypeptide to form a home dimeric protein of the invention; and/or (ii) the association of the GST subunit polypeptide of the invention with a non-identical GST subunit to form a heterodimeric protein of the invention.

and preferably (b) recovering the dimeric proteins so formed, and optionally resolving them.

Where only a single type of GST subunit-encoding sequence of the invention is present in the transformed cell, these processes normally give rise to homodimeric proteins of the invention. Where one or more further GST subunit-encoding sequences is present, these processes give rise to heterodimers or to a mixture of some or all of the following: homodimers of each possible type.

Alternatively, dimeric proteins of the invention can be produced by expressing the required polypeptide subunits in separate cells. This typically leads to the production of two different types of homodimer. The desired heterodimer can then be prepared by: mixing the homodimers and denaturing the mixed sample, or by denaturing the homodimers separately and then mixing them; then renaturing the mixed sample. This will typically lead to a mixture of dimeric proteins comprising both possible types of homodimers and also heterodimers comprising one subunit of each type. Similarly, mixtures of greater numbers of types of dimer can be produced in this way if different homodimers are produced in three or more different cells, or if cells that give rise to heterodimers are used.

For these processes, any transformed cell as described above may be used. Bacterial cells are preferred, especially cells of *E. coli*, although other cell types may also be used.

Optionally, the polypeptide or dimeric protein may be isolated and/or purified, by techniques known in the art.

In processes of the invention, any suitable method may be used to denature and/or renature polypeptides of the invention, and suitable methods are well known in the art.

Similarly, where a mixture of polypeptide subunits or dimeric proteins results, these may be resolved or separated by any suitable technique known in the art.

Antibodies

The invention also provides monoclonal or polyclonal antibodies which specifically recognise polypeptides of the invention or dimeric proteins of the invention.

Thus, antibodies of the invention bind specifically to the polypeptides and/or dimers of the invention, preferably to the extent that they distinguish between the polypeptides and/or dimers of the invention and other GST subunits and GSTs.

Monoclonal antibodies may be prepared by conventional hybridoma technology using polypeptides or dimeric proteins of the invention as immunogens. Polyclonal antibodies may also be prepared by conventional means which comprise inoculating a host animal, for example a rat or a rabbit, with a polypeptide of the invention and recovering immune serum. In order that such antibodies may be made, polypeptides may be haptenised to another polypeptide for use as immunogens in animals or humans. For the purposes of this invention, the term "antibody" includes antibody fragments such as Fv, F(ab) and F(ab)$_2$ fragments, as well as single chain antibodies.

Methods of producing Transgenic Plant Cells, Plant Parts and Tissues, Slants and Seeds of the Invention Transgenic plant cells, plant parts and tissues, plants and seeds of the invention are transgenic in the sense that they have at least one polynucleotide of the invention introduced into them.

The invention provides a method of obtaining a transgenic plant cell comprising transforming a plant cell with an expression vector of the invention to give a transgenic plant cell; and optionally transforming the cell with one or more further polynucleotide sequences coding for a GST subunit, operably linked to regulatory elements that allow expression of the subunit in the cell.(As discussed above, this allows the production of heterodimeric GST dimers of the invention, or the production of homodimeric ones of the invention in greater quantities.)

Any suitable transformation method may be used, for example the transformation techniques described herein. Preferred transformation techniques include electroporation of plant protoplasts, transformation by *Agrobacterium tumefaciens* and particle bombardment. Particle bombardment is particularly preferred for transformation of monocot cells.

The cell may be in any form, for example, it may be an isolated cell, e.g. a protoplast, or it may be part of a plant tissue, e.g. a callus, or a tissue excised from a plant, or it may be part of a whole plant. Transformation may thus give rise to a chimeric tissue or plant in which some cells are transgenic and some are not.

Preferably, integration of a polynucleotide or chimeric gene of the invention into the cell's genome is achieved.

The thus obtained cell may be regenerated into a transgenic plant by techniques known in the art. These may involve the use of plant growth substances such as auxins, giberellins and/or cytokinins to stimulate the growth and/or division of the transgenic cell. Similarly, techniques such as somatic embryogenesis and meristem culture may be used.

In many such techniques, one step is the formation of a callus, i.e. a plant tissue comprising expanding and/or dividing cells. Such calli are a further aspect of the invention as are other types of plant cell cultures and plant parts. Thus, for example, the invention provides transgenic plant tissues and parts, including embryos, meristems, seeds, shoots, roots, stems, leaves and flower parts. These may be chimeric in the sense that some of their cells are transgenic and some are not.

Regeneration procedures will typically involve the selection of transformed cells by means of marker genes. Some marker genes have already been mentioned and it should also be noted that the polynucleotides of the invention can themselves act as marker genes if they are under the control of regulatory sequences that allow their expression during the appropriate stage of the regeneration procedure. The polypeptides of the invention are capable of conferring resistance to herbicides or other phytotoxic compounds which are detoxified by GSTs on cells of the invention, as described below. Thus, an appropriate herbicide can be used to select transformants.

The regeneration step gives rise to a first generation transgenic plant. The invention also provides methods of obtaining transgenic plants of further generations this first generation plant. These are known as progeny transgenic plants, progeny plants of second, third fourth, fifth, sixth and further generations may be obtained from the first generation transgenic plant by any means known in the art.

Thus, the invention provides a method of obtaining a transgenic progeny plant comprising obtaining a second-generation transgenic progeny plant from a first-generation transgenic plant of the invention, and optionally obtaining transgenic plants of one or more further generations from the second-generation progeny plant thus obtained.

Such progeny plants are desirable because the first generation plant may not have all the characteristics required for cultivation. For example, for the production of first generation transgenic plants, a plant of a taxon that is easy to transform and regenerate may be chosen. It may therefore be necessary to introduce further characteristics in one or more subsequent generations of progeny plants before a transgenic plant more suitable for cultivation is produced.

Progeny plants may be produced form their predecessors of earlier generations by any known technique. In particular, progeny plants may be produced by:

obtaining a transgenic seed from a transgenic plant of the invention belonging to a previous generation, then obtaining a transgenic progeny plant of the invention belonging to a new generation by growing up the transgenic seed;

and/or propagating clonally a transgenic plant of the invention belonging to a previous generation to give a transgenic progeny plant of the invention belonging to a new generation;

and/or crossing a first-generation a transgenic plant of the invention belonging to a previous generation with another compatible plant to give a transgenic progeny plant of the invention belonging to a new generation;

and optionally;

obtaining transgenic progeny plants of one or more further generations from the progeny plant thus obtained.

These techniques may be used in any combination, for example, clonal propagation and sexual propagation may be used at different points in a process that gives rise to a transgenic plant suitable for cultivation. In particular, repetitive back-crossing with a plant taxon with agronomically desirable characteristics may be undertaken. Further steps of removing cells from a plant and regenerating new plants therefrom may also be carried out.

Also, further desirable characteristics may be introduced by transforming the cells, plant tissues, plants or seeds, at any suitable stage in the above process, to introduce desirable coding sequences other than the polynucleotides of the invention, this may be carried out by the techniques described herein for the introduction of polynucleotides of the invention.

For example, further transgenes may be selected from those coding for other herbicide resistance traits; e.g. tolerance to Glyphosate (e.g. using an EPSP synthase gene (e.g. EP-A-0 293,358) or a glyphosate oxidoreductase (WO 92/000377) gene); or tolerance to fosametin; a dihalobenzonitrile; glufosinate (e.g. using a phosphinotricyine acetyl transferase or glutamine synthase gene (cf. EP-A0 242,236); asulam (e.g. using a dihydropteroate synthase gene (EP-A-0 369,367); or a sulphonylurea (e.g. using an ALS gene); diphenyl ethers such as acifluorfen or oxyfluorfen (e.g. using a protoporphyrogen oxidase gene); an oxadiazole such as oxadiazon; a cyclic imide such as chlorophthalim; a phenyl pyrrazole such as TNP, or a phenopylate or carbamate analogue thereof.

Similarly, genes for beneficial properties other than herbicide tolerance may be introduced. For example, genes for insect resistance may be introduced, notably genes encoding *Bacillus thuringiensis* (Bt) toxins.

Transgenic Plant Cells, Plant Parts and Tissues, Plants and Seeds of the Invention The invention also provides transgenic plant cells, plant parts and tissues, plants and seeds, these are typically obtainable, or obtained, by the methods described above. They may be of any botanical taxon, e.g. any species or lower taxonomic grouping. Preferably, they are of a crop pant species.

Transgenic plant cells, plant parts and tissues, plants and seeds of the invention may thus be of a monocotyledonous (monocot) or dicotyledonous (dicot) taxon. Preferred dicot crop plants include tomato; potato; sugarbeet; cruciferous crops, including oilseed rape; linseed; tobacco; sunflower, fibre crops such as cotton; and leguminous crops such as peas, beans, especially soybean, and alfalfa Preferred monocots include graminaceous plants such as wheat, maize, rice, oats, barley and rye, sorghum, triticale and sugar cane. Wheat is particularly preferred.

Typically, a polypeptide of the invention is expressed in a plant of the invention. depending on the promoter used, this expression may be constitutive or inducible, e.g. by a herbicide safener. similarly, it may be tissue- or stage-specific, i.e. directed towards a particular plant tissue or stage in plant development.

Preferably, plant cells, plant parts and tissues, plants and seeds of the invention exhibit herbicide resistance due, at least in part, to expression of a polypeptide of the invention.

Herbicides to which plants of the invention may be resistant include Fluorodifen, Fenoxaprop-ethyl, Metolachlor, Alpha-Metolachlor, Acetochlor, Alachlor, Pretilachlor, Fluthiamid, Dimethenamid, S-Dimethenamid, Flupyrsulfuron-methyl, Triflusulfuron-methyl, Acifluorfen, Chlorimuron-ethyl, Fomesafen, Atrazine, Simazine, Cyanazine, and Metribuzin. Particularly preferred herbicides include Fenoxaprop-ethyl, Flupyrsulfuron-methyl, Fluthiamid, Acetochlor, Metolachlor and Alpha-Metolachlor. Plants of the invention may also exhibit resistance to other herbicides capable of conjugation to GSH by GSTs or to other non-herbicide phytotoxic substances.

Preferably, a transgenic plant of the invention exhibits resistance to one or more of Fenoxaprop-ethyl, Flupyrsulfuron-methyl, Fluthiamid, Acetochlor, Metolachlor and Alpha-Metolachlor. Resistance may be exhibited to herbicides which are selective for particular plant taxa and/or herbicides which are generic to all plants.

Uses of the Polynucleotides, Polypeptides, Antibodies, Probes and Plants of the Invention Apart from enabling the generation of herbicide-resistant plants, the invention has a number of other uses.

Selectable Markers

Polynucleotides of the invention can be used as selectable markers for detecting the transformation of plant cells. When expressed from polynucleotides of the invention, the polypeptides of the invention are capable of conferring herbicide resistance on cells of the invention, as described herein. Thus, an appropriate herbicide can be used to select transformants.

Accordingly, the invention provides-a nucleic acid construct comprising:
 (a) a polynucleotide of the invention operably linked to regulatory elements that allow expression of a polynucleotide of the invention a plant cell; and
 (b) a site into which a further polynucleotide comprising a coding sequence can be inserted.

Preferably, site (b) is bounded by regulatory elements that allow expression of a coding sequence inserted at the site in a plant cell.

These constructs may be contained within vectors as described herein.

In these constructs, site (b) is a site into which another nucleic acid sequence can be inserted. in cells transformed with the constructs or vectors containing them, expression of the polypeptide of the invention can be used as a selectable marker, indicating that the polynucleotide at site (b) has also been successfully introduced.

In this connection, the invention also provides a method of transforming a plant cell or of obtaining a plant cell culture or transgenic plant comprising:
 (a) providing an untransformed plant cell which is susceptible to a herbicide whose herbicidal activity is reduced by a dimeric protein of the invention;
 (b) transforming the plant cell with a vector comprising a marker construct of the invention;
 (c) cultivating the transformed cell under conditions that allow the expression of a polypeptide of the invention; and /or
 (c') regenerating the cell to give a cell culture or plant such that a polypeptide of the invention is expressed;
and
 (d) contacting the cell, cell culture or plant with the herbicide whose herbicidal activity is reduced by a dimeric protein of the invention, and to which herbicide the untransformed plant cell was susceptible;
and
 (e) selecting cells, cell cultures or plants that are less susceptible to the herbicide than are corresponding untransformed cells, cell cultures or plants.

Identification of Novel Herbicides

The polypeptides and dimeric proteins of the invention may be used to identify compounds capable of conjugation to GSH. Thus, as conjugation to GSH is the mechanism by which GSTs are believed to effect detoxification of herbicides, the polypeptides of the invention can be used to determine whether or not a candidate herbicidal compound will be detoxified by GSTs, for example the dimeric proteins of the invention. In this case, it may be possible to develop the candidate compound as a herbicide. In particular, it may be possible to develop the candidate compound for selective use as a herbicide on crops of wheat, or of a wheat-related species, or of other plants (cf Feldman et al supra), having GSTs with similar activity to the dimeric proteins of the invention. This is because species having such GSTs can be expected to detoxify herbicides identified in the assay.

Accordingly, the invention provides a method of identifying compounds capable of conjugation to glutathione comprising:
 (a) contacting a candidate compound suspected of being capable of being metabolised by glutathione transferase with glutathione (GSH) in the presence of a dimeric protein of the invention; and
 (b) determining whether or not metabolism of the candidate compound takes place, or to what extent takes place.

Preferably, metabolism of the compound is detected by determining whether, or to what extent, conjugation of the candidate compound to GSH takes place.

Such assay methods may be carried out by any suitable means known in the art. Compounds may be assayed singly, or, preferably, in batches containing several compounds. For example, microtitre plate-based assay techniques may be used. More specifically, the techniques of Example 4 below may be used.

The invention also provides compounds identified by the methods of the invention.

The invention also provides a kit for detecting compounds capable of being metabolised by a GST comprising:
 (a) reduced glutathione, hydroxymethylglutathione or homoglutathione; and
 (b) a dimeric protein of the invention.

Such kits may also comprise other components, especially buffer solutions, e.g. aqueous solutions buffered at a suitable pH (e.g. pH7 to pH10, preferably pH7 to pH8).

These kits can be used in the identification of novel herbicides.

Identification of Compounds that Induce GST Expression

We have found that expression of the GSTs of the invention is induced by herbicide safeners. As GSTs are implicated in herbicide resistance, it may be desirable to identify other compounds capable of inducing their expression or that of related GSTs in wheat or other plants, preferably graminaceous plants. Such compounds may, for example, be used to induce expression of GSTs involved in herbicide tolerance. This will be beneficial as it will allow crop plants to be selectively protected from herbicides whilst weeds are killed by them.

Accordingly, the invention provides a method of identifying compounds that induce GST expression in graminaceous plants comprising:

(a) contacting a plant, preferably a graminaceous plant, or a cell or cell culture thereof, with a candidate compound suspected of being capable of inducing GST expression; and (b) determining the level of GST expression in the plant, cell or cell culture.

Typically, the level of expression is also determined before the compound is added, or in an untreated sample, in order to provide a control. If the level of GST expression in the test sample is higher than that in the control sample then the candidate compound is an inducer of GST expression.

Preferably, the level of GST expression is determined quantitatively although, in certain situations, quantitative detection may suffice, e.g. where the level of expression is zero or undetectable in the absence of an inducer.

Determination of the level of GST expression may be performed by any suitable means. Preferably, it is performed using antibodies or probes of the invention, as described herein.

The invention also provides compounds identified by these methods.

Antibodies that specifically recognise the polypeptides or dimeric proteins of the invention can be used to detect and preferably quantify GST expression by detecting them directly. The antibodies of the invention may thus be used for detecting polypeptides or dimeric proteins of the invention present in plant samples, e.g. by a method which comprises:

(a) providing an antibody of the invention;

(b) incubating a plant sample with said antibody under conditions which allow for the formation of an antibody-antigen complex; and (c) determining, by any suitable technique known in the art, whether antibody-antigen complex comprising said antibody is formed.

Antibodies of the invention may be bound to a solid support and/or packaged into kits in a suitable container along with suitable reagents, controls, instructions and the like.

Similarly, polynucleotides or primers of the invention or fragments thereof, labelled or unlabelled, may be used by a person skilled in the art in nucleic acid-based tests for detecting nucleic acid sequences of the invention in a sample taken from a plant, typically a wheat plant.

Such tests generally comprise bringing a sample containing DNA or RNA into contact with a probe comprising a polynucleotide or primer of the invention under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe.

Alternatively, the sample nucleic acid may be immobilised on a solid support, and the amount of probe bound to such a support can be detected.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridising the probe to nucleic acid in the sample, control reagents, instructions, and the like.

Measuring the Level of GST in Batches of Seed or Flour

Owing to the secondary activity of the GSTs of the invention as glutathione peroxidases, the polypeptides and dimeric proteins of the invention will also have applications in determining the quality of batches of seed and flour, especially of wheat seed, grain and wheat flour. In such batches, glutathione peroxidases are involved in reducing lipid hydroperoxides, which reduces the amount of GSH available. In particular, this occurs during bread making. Thus, it is desirable to be able to monitor the level of GSTs having glutathione peroxidase activity in batches of seed and flour.

This can be done by any suitable means. For example, antibodies of the invention can be used to detect polypeptides or dimeric proteins of the invention, as described above. Similarly, probes of the invention can be used to detect GST mRNA, as described above.

Alternatively, to determine directly the level of GSH in a batch, the invention provides a method of determining the GSH level in a batch of seed or flour comprising:

(a) contacting a sample from the batch with a polypeptide or dimeric protein of the invention and a compound whose conjugation to GSH is catalysed by the polypeptide or protein; and (b) determining the GSH level from the extent of reaction between the compound and GSH.

Controlling the Growth of Weeds

The invention also provides a method of controlling the growth of weeds at a locus where a transgenic plant of the invention is being cultivated, which method comprises applying a herbicide to the locus. Any amount of herbicide may be used, as long as it is herbicidally effective against the weeds but leaves the herbicide resistant plants of the invention unaffected, or substantially unaffected. The effect on the weeds may be, for example, to kill them or to inhibit their growth.

Any type of weed that responds to a particular herbicide may be controlled in this way. *Alopecurus myosuroides, Avena fatua*, Lolium spp., Bromus spp., *Poa annua, Galium aparine, Aper spica-venti, Matricaria inodora, Stellaria media, Papaver rhoeas*, Polygonum spp., Setaria sp., *Sorghum halapense, Panicum miliaceum*, Echinochloa spp., *Digitaria sanguinalis, Phalaris minor, Abutilon theophrasti, Amaranthus retroflexus, chenopodium album, Datura stramoniuon Solanum nigrum, Xanthium strumarium, saggitaria* spp., *Monochoria vaginalis*, Lindernia spp., *Eleokaris kurogaai, Scirpus juncoides*, Cyperus spp.

The herbicide may, for example, be one whose activity is identified by the methods of the invention (see above). Alternatively, it may be a known herbicide, for example one of the herbicides mentioned herein.

The herbicide may be applied at any suitable time during the life cycle of the transgenic plant, for example pre-emergence or post-emergence. Timing of application will be tailored to the development of the weeds which it is desired to control. Where inducible or tissue- and/or stage-specific expression of the active dimer of the invention is employed, timing of herbicide application will be tailored to the optimal expression of the invention in the course of the development of the transgenic plant of the invention.

The following Examples illustrate the invention.

EXAMPLES

Example 1

Isolation and Characterisation of the Nucleotide Sequence 1 Encoding TaGST1

(a) Purification of Wheat GST Isoenzymes

Wheat GST isoenzymes containing the TaGST1 subunit were purified by the method of Dixon et al (Pestic. Sci. 1997, 50, 72–82). This is summarised below.

Wheat seeds (*Triticum aestivum L.* var. Hunter) were imbibed in a 10 mg/l solution of the herbicide safener fenchlorazole-ethyl and then grown in an environmental growth room with further root-applied watering treatments of 5 mg/l fenchlorazole ethyl applied as required. At 10 days after imbibing, the shoot tissue was harvested and extracted prior to precipitation of the protein with ammonium sulphate (80% saturation). The total protein extract was then applied in the presence of 1 M ammonium sulphate to a phenyl-Sepharose column. The bound GSTs were then recovered, firstly by reducing the ammonium sulphate concentration to 0 M to yield the polar GST fraction, which represented 61% of the recovered activity toward 1-chloro-2,4-dinitrobenzene (CDNB). The remaining 39% of the GST activity was then recovered by adding ethylene glycol (50% v/v) to the running buffer to yield the hydrophobic GST fraction.

The polar and hydrophobic GST fractions were then independently applied to the affinity matrix, S-hexyl-glutathione agarose. This matrix bound 90% of the GST activity toward CDNB. Prior to elution of the column with the ligand, S-hexyl-glutathione, the matrix was washed with phosphate buffer, followed by phosphate buffer containing 200 mM potassium chloride. The GSTs eluting in this salt wash were termed the "loosely-bound" fraction. Tightly-bound proteins were then eluted with 5 mM S-hexyl-glutathione. With both the polar and hydrophobic GSTs an average of 34% of the GST activity toward CDNB eluted in the loosely-bound fraction and 66% eluted in the presence of S-hexyl-glutathione. The loosely-bound fraction contained the GSTs which will be considered in Example 2. The major wheat GSTs of interest in this example were found in the affinity-purified pool and to define the numbers of isoenzymes and component subunits present, this pool was analysed in detail.

Figure 1B:
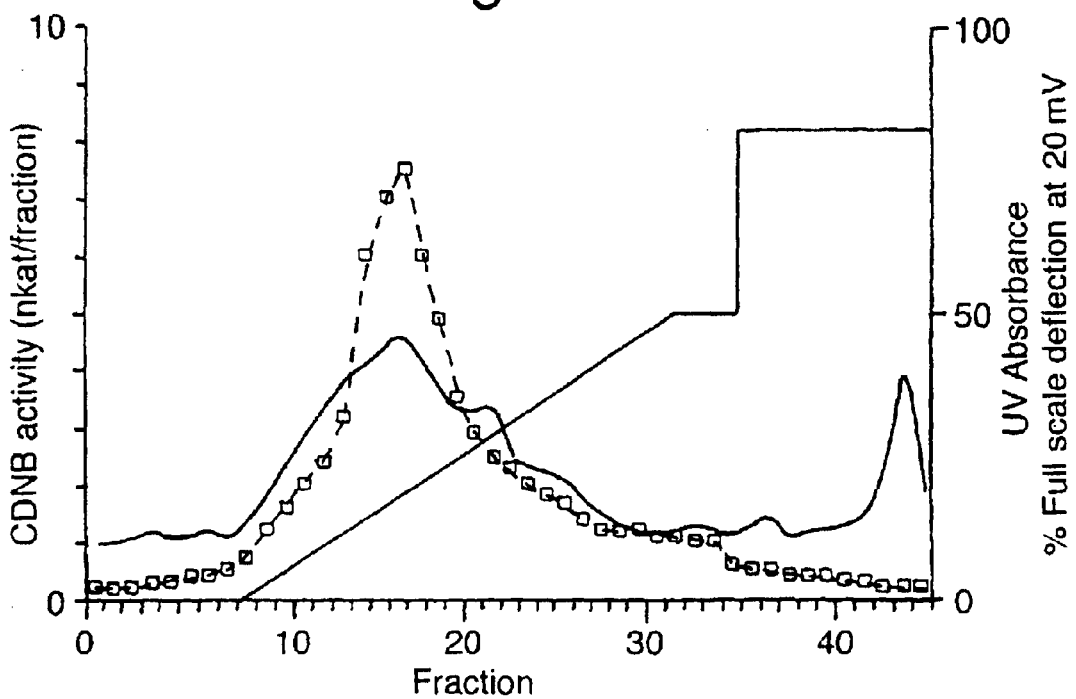

When the affinity-bound pools of the polar and hydrophobic GSTs were analysed by anion-exchange chromatography on Q-sepharose, the partial resolution of the eluting activity suggested the presence of multiple isoenzymes (FIG. 1). The component polypeptides in the active fractions were then analysed by silver staining after resolution by sodium dodecyl sulphate polyacrylamide gel electrophoresis (SDS-PAGE). It was concluded that in fenchlorazole-ethyl-treated wheat the polar GSTs were composed of 25 kDa and 26 kDa polypeptides, while the hydrophobic fraction contained 25 kDa, 26 kDa and 24 kDa polypeptides. Further analysis by reversed-phase HPLC confirmed the subunit compositions (FIG. 2). Based on the combined analyses by Q-sepharose, HPLC and SDS-PAGE these GST polypeptides were named as described in Table 1, which also contains details of how these subunits associate together to form the active dimers found in plants and the relative abundance of these subunits in extracts from unsafened and fenchlorazole-ethyl treated (safened) plants.

(b) GST Activities of the Purified TaGST Isoenzymes

The purified isoenzymes were assayed for GST activity toward herbicides using the HPLC-based assays described by Edwards R. and Cole D. J. (Pesticide Biochemistry and Physiology Vol. 54, pp96–104 (1996)) and the results are presented in Table 2. Both polar and hydrophobic GSTs from the affinity-bound pools of isoenzymes showed detoxifying activities toward the selective graminicide fenoxaprop-ethyl, the diphenyl-ether herbicide fluorodifen, and the chloracetanilide metolachlor. These isoenzymes had additional activities as glutathione peroxidases able to reduce linoleic acid hydroperoxide, a major reaction product formed during membrane peroxidation in plants (Williamson and Beverly. J. Cereal Sci. 8, 1988, 155–163).

(c) Preparation of Polyclonal Antibodies to the Major Wheat GST Isoenzymes

Purified TaGST1-1 was used to immunise rabbits to raise polyclonal antibodies to the differing isoenzymes. The reactivity of the antiserum toward crude wheat preparations was demonstrated with a Western blot of polypeptides resolved by SDS-PAGE. The antibodies were then used to identify the corresponding cDNAs in an expression library.

(d) Identification and Characterisation of a cDNA Encoding TaGST1

An expression library was prepared from poly (A)+ RNA extracted from 7-day wheat shoots grown from seed treated with fenchlorazole-ethyl. The library was constructed in lambda ZAP II (Stratagene) and plaque forming units (pfus) screened with the antiserum raised against TaGST1-1. From an initial screen of 170,000 pfus 17 positive plaques were identified, of which 12 were further purified to homogeneity in secondary and tertiary screens and the wheat cDNAs excised from the phage to form Bluescript plasmids in *E. coli* SOLR. (Stratagene). Automated DNA sequencing showed that all clones had an identical coding sequence, although differences in the 5' and 3' untranslated regions were apparent, such that of 6 clones sequenced fully on both strands, 4 different untranslated regions were observed. Since these clones shared a common open reading frame they were all designated TaGST1 and then subdivided as A, B, C and D. The nucleotide sequence of TaGST1 showing the variable untranslated regions of A, B, C and D is shown in SEQ ID No. 1, together with the deduced amino acid sequence of the coding region (SEQ ID No. 2).

To confirm that TaGST1 encoded a GST, it was expressed as a fusion protein with beta-galactosidase using the pBluescript plasmid in *E. coli* strain SOLR. TaGST1 clones were inoculated into LB liquid medium and were grown overnight at 37/C on all orbital shaker in the presence of IPTG. Bacteria were then pelleted by centrifugation, lysed by sonication and assayed for GST activity toward CDNB and analysed by SDS-PAGE and Western blotting using the anti-TaGSTI-I serum. With all six TaGST1 clones, GST activity toward CDNB could be determined in the crude extracts in the range 30–50 nkat/mg crude lysate. This was in contrast to control *E. coli* containing the bluescript plasmid without a cDNA insert which showed negligible GST activity (0.2 nkat/mg. When the polypeptides contained in the lysates of the various TaGST1 clones were analysed by SDS-PAGE, in every case the TaGST1-fusion protein was clearly visible as a highly expressed polypeptide relative to the controls. All the fusion proteins reacted with the anti-TaGST1 serum.

To confirm that the GST activity in the extracts from TaGST1 clones was due to the fusion protein, the GST-fusion was purified using S-hexyl-glutathione agarose affinity chromatography. The pure fusion protein was then assayed for enzyme activity toward herbicide and hyproperoxide substrates and was found to show a similar spectrum of activities to that of the pure TaGST1-1 isoenzyme from wheat shoots.

TABLE 1

Summary of the characteristics of major classes of wheat GST isoenzymes. The GST subunits had the following retention times by reversed-phase HPLC. TaGST1a - 26.4 min, TaGST1b - 27.1 min, TaGST2 - 31.1 min, TaGST3 - 30.9 min, TaGST4 - 33.2 min.

| ISO-ENZYME TYPE | SUB-UNITS | POLAR (P) OR HYDRO-PHOBIC (H) | MOLE-CULAR WEIGHT (KDA) | ANTI-TAGST1 ANTIBODY REACTION | % EN-HANCE-MENT BY SA-FENER |
|---|---|---|---|---|---|
| TaGST1-1 | TaGST1a | P | 25 | + | 30–50 |
|  | TaGST1b | P | 25 | + | 30–50 |
| TaGST1-2 | TaGST1a | P | 25 | + | Only observed with safener |
|  | TaGST1b | P | 25 | + |  |
|  | TaGST2 | P | 26 | − |  |
| TaGST1-3 | TaGST1a | P | 25 | + | Only observed with safener |
|  | TaGST1b | P | 25 | + |  |
|  | TaGST3 | H | 26 | − |  |
| TaGST1-4 | TaGST1a | P | 25 | + | 300% |
|  | TaGST1b | P | 25 | + | 300% |
|  | TaGST4 | H | 24 | − | 300% |

TABLE 2

Activity of GST isoenzymes purified from fenchlorazole-ethyl-treated wheat shoots. Enzyme activities are expressed as $nkat.mg^{-1}$

| ISOENZYME | CDNB | FLUORO-DIFEN | FENOXAPROP-ETHYL | METO-LACHLOR |
|---|---|---|---|---|
| Polar |  |  |  |  |
| TaGST1-1 | 1,528 | 0.97 | 0 | 0.11 |
| TaGST1-2 | 1,441 | 0.38 | 0.61 | 0.25 |
| Hydrophobic |  |  |  |  |
| TaGST1-3 | 1,700 | 0.38 | 0.44 | 0.28 |
| TaGST1-4 | 1,553 | 0.57 | 0.23 | 0.23 |

TABLE 3

CDNB and herbicide activities of recombinant wheat GSTs Activities expressed as $nkat.mg^{-1}$ ± standard error

| RECOMBINANT ENZYME | CDNB | FLUORO-DIFEN | FENOXAPROP-ETHYL | METO-LACHLOR |
|---|---|---|---|---|
| TaGST1 | 1970 ± 30 | 2.0 ± 0.1 | 0 | 0.127 ± 0.014 |
| WIC 1 | 406.5 ± 0.5 | 0.136 ± 0.011 | 0.050 ± 0.010 | 0.315 ± 0.003 |
| WIC 2 | 187 ± 1 | 0.096 ± 0.002 | 0.085 ± 0.002 | 0.512 ± 0.04 |
| WIC 3 | 2,519 ± 88 | 0.014 ± 0.006 | 0.093 ± 0.002 | 0.053 ± 0.004 |
| WIC 4 | 980 ± 86 | 0.036 ± 0.004 | 0.012 ± 0.001 | 0.037 ± 0.003 |
| WIC 5 | 174 ± 8 | 0.030 ± 0.002 | 0.067 ± 0.003 | 0.040 ± 0.004 |
| TA 27 | 237 ± 13 | 0.034 ± 0.003 | 0.036 ± 0.004 | 0.063 ± 0.006 |
| ICR | 8139 ± 146 | 0.037 ± 0.002 | 0.028 ± 0.001 | 0.000 ± 0.000 |
| ICC/V/P | 30 ± 4 | 0.000 ± 0.000 | 0.074 ± 0.008 | 0.000 ± 0.000 |

Example 2

Cloning of Wheat GSTs Resembling the Type I GSTs from Maize (a) Characterisation of Type I GSTs in Wheat The observation that extracts from safener-treated wheat shoots contained GSTs which, unlike those described in Example 1, were not selectively retained on the affinity matrix suggested that a discrete class of GSTs were present in this loosely bound fraction. Crude extracts of wheat seedlings were analysed by Western blotting following SDS-PAGE using a polyclonal rabbit antiserum raised to the type I ZmGSTI-II heterodimer. The antiserum reacted strongly with several polypeptides of Mr 23–27 kDa. These polypeptides were present in the loosely-bound fraction from the S-hexyl-glutathione affinity column, but not in the affinity bound fraction.

(b) Cloning of cDNAs from a Wheat Expression Library

Having established that safener-treated wheat shoots contained polypeptides which cross-reacted with the antiserum raised to the maize GSTs, the primary cDNA expression library prepared from fenchlorazole-ethyl treated wheat shoots was screened with the antibody for positive clones. Following a screen of 170,000 pfu., ten positive plaques were identified, with obvious differences in the intensity of recognition, with four plaques showing a strong colour reaction and six plaques of lower intensity. These cDNA clones were termed WIC clones. All four of the stronger-reacting plaques (WIC 1, 2, 4 and 5) and four of the weaker positives (WIC 3, 7, 8 and 10) were purified to homogeneity, the respective plasmids excised and DNA preparations sequenced. The clones were then grouped by their degree of similarity in sequence.

In the sequence listing, WIC 1 is SEQ ID No. 3 and its deduced amino acid sequence is SEQ ID No. 4. WIC 2 is SEQ ID No. 5 and its deduced amino acid sequence is SEQ ID No. 6. The coding sequences of WIC 3, WIC 7 and WIC 8 were identical in sequence. The DNA sequence of WIC 3/7/8 is given in SEQ ID No. 7 and the deduced amino acid sequence in SEQ ID No. 8 All three sequences contained a stop codon in the 5' untranslated region of the GST gene, although some expression occurred. The DNA sequence of WIC 5 is shown in SEQ ID No. 9, and the deduced amino acid sequence in SEQ ID No. 10. WIC 4 and WIC 10 had identical coding sequences, but differed in their untranslated regions. In particular, WIC 10 had a stop codon in the 5' untranslated region, though this did not prevent all expression of the fusion protein The WIC 4 DNA sequence is given in SEQ ID No. 11 and the deduced WIC 4/10 amino acid sequence in SEQ ID No. 12 (the WIC 10 DNA sequence is not shown).

(c) Cloning of Wheat GSTs by Differential Screening of a cDNA Library

A further cDNA clone, termed TA 27 was obtained. A cDNA library prepared from wheat seedlings treated with the herbicide safener cloquintocet-mexyl, was screened for clones which represented mRNAs which were differentially expressed in wheat in response to safener application. The identity of the clone as a GST was suggested from its nucleotide (SEQ ID No. 13) and deduced amino acid (SEQ ID No. 14) sequence. As the coding sequence of TA 27 was not in frame with beta-galactosidase in the pBluescript vector, the coding sequence was sub-cloned into the expression vector pET 11a (Novagen), with translation starting at the first ATG codon in the clone, which gave a reasonable alignment of the open reading frame with that of other GSTs involved in herbicide metabolism, notably the ZmGSTIV sequence.

(d) Activity of Recombinant GSTs of the Invention

To confirm that the WIC clones and TA 27 encoded functional GSTs the corresponding enzymes were expressed as recombinant enzymes in E. coli. The full coding sequence of TA 27 was expressed in the pET vector, while the WIC clones were expressed as fusions with part of the beta-galactosidase enzyme using the pBluescript vector. The levels of recombinant protein expressed varied between the differing clones. Appreciable amounts of recombinant protein were observed in the TA 27 pET clones and in clones WIC 1, WIC 2, WIC 4 and WIC 5. Western blotting of these total bacterial extracts with the antiserum raised to ZmGSTI-II showed that the fusion proteins were selectively recognised by the antiserum. In contrast, use of the antiserum demonstrated much lower levels of expression of immunoreactive fusion proteins in clones WIC 3, WIC 7, WIC 8 and WIC 10.

To assay the recombinant fusion proteins for GST activity, the E. coli were grown in the presence of IPTG and then pelleted by centrifugation. The bacteria were then lysed by sonication and the protein precipitated using 80% ammonium sulphate. After resuspension and desalting, GSTs were purified by affinity chromatography. The WIC 3 fusion protein was purified using sulphobromophthalein-S-glutathione affinity chromatography (Mozer et al. Biochem. 22, 1983, 1068–1072) while the other WIC fusion proteins were purified using glutathione-agarose (Mannervik and Guthenberg. Methods Enzymol. 77 1981, 231–235).The purified enzymes were then assayed for GST activities toward herbicides (Table 3) and GST activities toward non-herbicide substrates and glutathione peroxidase activities toward organic hydroperoxides (Table 4).

TABLE 4

Other GST activities and glutathione peroxidase activities.
Activities expressed as nkat.mg$^{-1}$ ± standard error.
Peroxidase activities expressed as absorbance change at
340 nm.mg$^{-1}$ ± standard error (n = 3).
N.D = not detected, — not performed.

| | CUMENE HYDRO-PEROXIDE | BENZYL ISOTHIO-CYANATE | CROTONAL-DEHYDE | ETHA-CRYNIC ACID |
|---|---|---|---|---|
| WIC 1 | 18.6 ± 0.5 | 18.0 ± 3.75 | 7.1 ± 0.7 | N.D. |
| WIC 2 | 28.2 ± 1.7 | 33.3 ± 4.5 | 5.5 ± 1.3 | N.D. |
| WIC 3 | 1.4 ± 0.3 | 9.0 ± 0.5 | 6.3 ± 0.9 | N.D. |
| WIC 4 | 6.2 ± 0.3 | 4.2 ± 0.4 | 5.5 ± 0.6 | 1.4 ± 0.3 |
| WIC 5 | 1.3 ± 0.2 | 9.4 ± 2.0 | 4.5 ± 0.5 | N.D. |
| TaGST1 | 0.7 ± 0.1 | 11.8 ± 0 | 3.7 ± 0.3 | N.D. |
| TA 27 | 3.6 ± 0.4 | — | — | — |

TABLE 4-continued

Other GST activities and glutathione peroxidase activities.
Activities expressed as nkat.mg$^{-1}$ ± standard error.
Peroxidase activities expressed as absorbance change at
340 nm.mg$^{-1}$ ± standard error (n = 3).
N.D = not detected, — not performed.

| | CUMENE HYDRO-PEROXIDE | BENZYL ISOTHIO-CYANATE | CROTONAL-DEHYDE | ETHA-CRYNIC ACID |
|---|---|---|---|---|
| ICR | N.D | — | — | — |
| ICC/V/P | 0.84 ± 0.04 | — | — | — |

Example 3

Cloning of Safener-inducible Type III GSTs from Wheat

A polyclonal antiserum was raised in a rabbit to a mixture of TaGST1-2 and TaGST1-3. When tested against crude extracts from safener-treated wheat shoots the antiserum recognised both the 25 kDa TaGST1 subunit and the 26 kDa safener-inducible TaGST2 and TaGST3 subunits. The antiserum was then used in conjunction with the antiserum raised to TaGST1-1 to immuno screen the cDNA library prepared from fenchlorazole ethyl treated wheat shoots as described in example 1. Duplicate lifts were taken from the plated out library and the first blot screened with the antiserum raised against TaGST1-2 and TaGST1-3. The second blot was screened with the antiserum raised to TaGST1-1. Five plaques were identified from the first blot which were absent from the second blot corresponding to cDNAs encoding TaGST2 or TaGST3 like polypeptides and theses clones were purified and the respective plasmids sequenced. One of the clones, termed ICJ had an identical nucleotide sequence to GST Ts1, a safener-inducible GST identified in Triticum tauschii (Riechers et al., 1997 Plant Physiol. 114, 1568). Another clone, ICR, though showing some similarity to ICJ had a novel coding DNA coding sequence (SEQ ID No. 15) and predicted amino acid sequence (SEQ ID No. 16). The other three clones ICC. ICP and ICV had identical DNA sequences (SEQ ID No. 17) and predicted amino acid sequence (SEQ ID No. 18). GST ICJ was sub-cloned into the pET 11a vector after using PCR to introduce a Nde 1 restriction site into the translation start site, using the primer 5' AGG TAG TTA CAT ATG GCC GGA GGA 3' (SEQ ID No. 19) in the amplification. following sub-cloning, the sequence of GST ICJ was re-checked to ensure no PCR induced errors had been introduced. The recombinant GST ICJ was then expressed in E. coli and purified by S-hexylglutathione affinity chromatography. The purified GST ICJ was assayed for activities as a GST (Table 3) and as a glutathione peroxidase (Table 4). The clone GST ICV was expressed in a variety of vectors, but in all cases the recombinant proteins proved impossible to purify using a variety of affinity columns (S-hexylglutathione-agarose, S-bromosulphophthalein glutathione agarose). GST ICV was finally expressed as the respective beta-galactosidase fusion protein using the Bluescript plasmid and assayed for GST activity (Table 3 ) and glutathione peroxidase activity (Table 4) in crude bacterial lysates. The specific activity of GST ICV toward these substrates was then calculated by I) subtracting the low levels of GST and GPOX activity present due the endogenous activities in the E. coli and ii) determining the proportion of protein in the lysate present as recombinant

Example 4

A Microtitre Plate—Based Screen to Identify Herbicidal Molecules Which are Metabolised by GSTs of the Invention and may Selectively Control Weeds in a Crop of Wheat or Other Species Such as Maize, Soybean or Rice

(a) Degradation of Candidate Herbicides by Wheat GSTs and Relationship to Crop and Weed Selectivity Herbicidal molecules which are degraded by recombinant wheat GSTs may be predicted to be tolerated by plants of wheat or other crop species. These herbicides may be less rapidly degraded in weeds such as black-grass (*Alopecurus myosuroides*) which are desirable to control in a crop of wheat or other species. Herbicides found in a laboratory based screen to be metabolised by these GSTs are therefore likely to possess useful abilities to selectively control troublesome weeds in a crop of wheat, or other species such as maize, soybean, rice, cotton, barley, oat, rye, sorhum, triticale, potato, sugarcane or sugarbeet.

(b) A 96 Well Plate—Based Assay Procedure for Identifying Novel Herbicides Degraded by Recombinant Wheat GSTs Novel herbicides arising from a chemical synthesis programme oriented to optimisation for selective herbicidal activity and potency may be screened for ability to be degraded by a panel of recombinant GSTs using a 96 well microplate assay format and subsequent reaction analysis by automated High Pressure Liquid Chromatography (HPLC). This allows for example, the screening of a set of eleven novel herbicides and one positive control compound such as CDNB, against a panel of seven recombinant GSTs. An eighth file of wells contains test compounds but lacks GSTs; these wells serve to identify non-enzymic reaction of the test compounds with reduced glutathione. Alternatively, the array can be configured to screen more test compounds against a more limited number of GSTs. For example, fifteen compounds can be screened against five GSTs or forty seven compounds may be screened with a single mixture of GSTs. In all cases, provision is made for a positive control and to test for non-enzymic reaction with reduced glutathione.

Enzyme assays are carried out in a total reaction volume of 100 microliters. Each reaction mixture contains 100 micromolar Tris.HCl buffer, pH 7:8, 500 micromolar reduced glutathione and where appropriate, 500 micromolar test compound or a reference substrate such as CDNB; and 14 micrograms of GST protein. The microplate is incubated at 30° C. on a variable speed agitator for 30 minutes and reactions are then stopped by the addition of 15 microliters of 23% perchloric acid solution, The microplate is then centrifuged at 2000 g for 15 minutes.

(c) Reaction Analysis by Automated High Pressure Liquid Chromatography.

The separation and analysis of glutathione conjugates of test herbicides may be carried out using High Pressure Liquid Chromatography (HPLC), for example a Gilson HPLC in tandem with corresponding software, for example Gilson Version 7.12 and fitted with an appropriate column, for example a 5 cm Spherisorb ODS2 column. Typically, separation may be carried out using a two phase solvent system as follows: Phase A: water containing 0.1% trifluoroacetic acid and 5.5% acetonitrile; Phase B: 100% acetonitrile; flow rate 1.5 ml per minute; injection volume 20 microliters.

The elution gradient may be typically as follows: 10% phase B for one minute, followed by a linear gradient to reach 60% phase B after 8.5 minutes. The gradient is further increased to reach 100% phase B at 9 minutes; phase B is continued at 100% until 11.5 minutes and is then reduced in a linear gradient to 10% at 13.5 minutes. A further 1.5 minutes at 10% phase B is required to re-equilibrate the column.

Absorbance signals are detected at 264 nanometers using a suitable UV detector, and detect the glutathione conjugate of CDNB, having a retention time of 2.4 minutes, resolving this from unreacted CDNB having a retention time of 4.75 minutes. Such conditions also allow for the resolution and detection of the glutathione conjugates arising from the metabolism of other reference herbicides such as metolachlor, fenoxaprop, fenoxaprop-ethyl and fluorodifen and also of a variety of novel herbicidal compounds identified in the assay.

What is claimed is:

1. An isolated polynucleotide encoding a glutathione transferase (GST) subunit, wherein the polynucleotide comprises the coding sequence of SEQ ID NO:1.

2. An isolated polynucleotide comprising a coding sequence encoding a glutathione transferase (GST) subunit, wherein the coding sequence encodes the amino acid sequence of SEQ ID NO:2.

3. The isolated polynucleotide of claim 2 or 1, wherein the polynucleotide is a DNA sequence.

4. A chimeric gene comprising the polynucleotide according to claim 2 or 1 operably linked to regulatory sequences that allow expression of the coding sequence in a host cell.

5. The chimeric gene according to claim 4 wherein the regulatory sequences allow expression of the coding sequence in a plant cell.

6. A vector comprising the polynucleotide according to any one of claims 2 to 4 or the chimeric gene according to claim 4 or 5.

7. The vector according to claim 6 which is an expression vector.

8. A host cell transformed with the vector according to claim 6.

9. The cell according to claim 8, wherein the cell is selected from the group consisting of a prokaryotic cell and a plant cell.

10. A host cell, having integrated into its genome, the chimeric gene according to claim 4.

11. The cell according to claim 10, wherein the cell is a plant cell.

12. A method of producing a transgenic plant cell comprising:
(a) transforming a plant cell with the expression vector according to claim 7 to produce a transgenic plant cell, and optionally,
(b) transforming the cell with one or more additional polynucleotide sequences coding for a GST subunit, operably linked to regulatory elements that allow expression of the subunit in the cell.

13. A method of producing a first-generation transgenic plant comprising:
(a) transforming a plant cell with the expression vector according to claim 7 to produce a transformed plant cell; and
(b) regenerating a first-generation transgenic plant from said transformed plant cell.

14. A first-generation transgenic plant produced by the method according to claim 13.

15. A method of producing a transgenic plant seed comprising:
(a) transforming a plant cell with the expression vector according to claim 7 to produce a transformed plant cell:
(b) regenerating a transgenic plant from said transformed plant cell; and
(c) producing a transgenic seed from the transgenic plant so produced.

16. A transgenic plant seed produced by the method according to claim 15, or a transgenic plant produced from said transgenic plant seed.

17. A method of producing a transgenic progeny plant from the first-generation transgenic plant produced by the method of claim 13 comprising serially propagating said first-generation transgenic plant through one or more successive generations to produce a second or successive generation transgenic progeny plant.

18. A transgenic progeny plant produced by the method of claim 17.

19. A transgenic plant cell produced by the method according to claim 12.

20. A transgenic plant cell callus comprising or produced from the plant cell according to claim 9 or claim 19.

21. A transgenic plant cell callus produced from the first generation transgenic plant of claim 14, the transgenic plant seed of claim 16 or the transgenic progeny plant of claim 18.

22. A nucleic acid construct comprising:
(a) the isolated polynucleotide according to claim 2 or 1 operably linked to regulatory elements that allow expression of the coding sequence in a plant cell; and
(b) a site into which as additional polynucleotide comprising a coding sequence can be inserted.

23. The nucleic acid construct of claim 22, wherein the site is flanked by regulatory elements that allow expression of a coding sequence inserted at the site in a plant cell.

24. A vector comprising the nucleic acid construct according to claim 22.

25. A method of producing transformed plant cells a transformed plant cell culture or transgenic plant, the method comprising:
(a) proving untransformed plant cells which are susceptible to a herbicide whose herbicidal activity is reduced by a dimeric protein comprising two GST subunits:
(b) transforming the plant cells with the vector according to claim 24;
(c) cultivating the transformed cells under conditions that allow the expression of the polynucleotide encoding a GST subunit;
(d) selecting transformed cells in the presence of said herbicide that are tolerant to said herbicide as compared to untransformed cells; and optionally
(e) producing cell cultures or regenerating plants from said transformed cells;
(f) contacting said cell cultures or plants with said herbicide; and
(g) selecting cell cultures or transgenic plants that are less susceptible to the herbicide than are corresponding untransformed cell cultures or plants.

26. A method of controlling the growth of weeds at a locus where the transgenic first-generation plant of claim 14, the transgenic plant seed of claim 16 or the transgenic progeny plant of claim 18 is being cultivated, said method comprising applying to said locus a herbicide whose herbicidal properties are reduced by a dimeric GST protein.

* * * * *